US009145560B2

(12) United States Patent
Baltimore et al.

(10) Patent No.: US 9,145,560 B2
(45) Date of Patent: Sep. 29, 2015

(54) METHOD FOR PRODUCING TRANSGENIC RATS

(75) Inventors: David Baltimore, Pasadena, CA (US); Elizabeth J. Hong, Bridgewater, NJ (US); Carlos Lois-Caballe, South Pasadena, CA (US); Shirley Pease, Monrovia, CA (US)

(73) Assignee: California Institute of Technology, Pasadena, CA (US)

( * ) Notice: Subject to any disclaimer, the term of this patent is extended or adjusted under 35 U.S.C. 154(b) by 1313 days.

(21) Appl. No.: 12/011,762

(22) Filed: Jan. 28, 2008

(65) Prior Publication Data

US 2008/0134352 A1 Jun. 5, 2008

Related U.S. Application Data

(63) Continuation of application No. 10/243,820, filed on Sep. 13, 2002, now Pat. No. 7,323,619.

(60) Provisional application No. 60/347,782, filed on Jan. 9, 2002, provisional application No. 60/322,031, filed on Sep. 13, 2001.

(51) Int. Cl.
*C12N 15/00* (2006.01)
*C12N 15/113* (2010.01)
*C12N 15/85* (2006.01)
*C12N 15/86* (2006.01)
*A61K 48/00* (2006.01)

(52) U.S. Cl.
CPC ........ *C12N 15/1138* (2013.01); *C12N 15/1132* (2013.01); *C12N 15/8509* (2013.01); *C12N 15/86* (2013.01); *A01K 2217/05* (2013.01); *A01K 2227/30* (2013.01); *A01K 2227/40* (2013.01); *A61K 48/00* (2013.01); *C12N 2740/16043* (2013.01); *C12N 2800/60* (2013.01); *C12N 2830/008* (2013.01); *C12N 2830/48* (2013.01); *C12N 2830/85* (2013.01); *C12N 2840/20* (2013.01); *C12N 2840/44* (2013.01)

(58) Field of Classification Search
USPC .......................................................... 800/21
See application file for complete search history.

(56) References Cited

U.S. PATENT DOCUMENTS

| | | | |
|---|---|---|---|
| 6,891,082 | B2 | 5/2005 | Lee et al. |
| 7,195,916 | B2 | 3/2007 | Qin et al. |
| 7,323,619 | B2 | 1/2008 | Baltimore et al. |
| 7,732,193 | B2 | 6/2010 | Lois-Caballe et al. |
| 7,732,207 | B2 | 6/2010 | Qin et al. |
| 7,737,124 | B2 | 6/2010 | Lois-Caballe et al. |
| 2003/0059944 | A1 | 3/2003 | Lois-Caballe et al. |
| 2003/0068821 | A1 | 4/2003 | Lois-Caballe et al. |
| 2003/0101472 | A1 | 5/2003 | Baltimore et al. |

FOREIGN PATENT DOCUMENTS

| | | |
|---|---|---|
| WO | WO 90/08832 | 8/1990 |
| WO | WO 00/29601 A | 12/2000 |
| WO | WO 03/056019 A | 7/2003 |

OTHER PUBLICATIONS

Schorpp et al., 1996, Nucleic Acids Research 24: 1787-1788.*
Chan (1998, PNAS, USA, 95: 029-14033).*
Zufferey (1998, Journal of Virology, 72: 9873-9880).*
Zufferey (1997, Nature Biotechnology, 15: 871-875).*
Naldini (1996, Science, 272: 263-267).*
Kilty (J. Neurochem., 1999, vol. 75, p. 1859-1870).*
Zufferey (1999, Journal of Virology, 2886-2892).*
van der Putten (1985, PNAS, USA, 82: 6148-6152).*
Linney et al., "Transgene Expression in Zebrafish: A Comparison of Retroviral-Vector and DNA-injection Approaches," *Developmental Biology* 213: 207-216 (1999).
Alper, Joe, "Hatching the Golden Egg; A New Way to Make Drugs", Science Magazine, May 2, 2003, p. 729-730, vol. 300, Louisville, Colorado.
Asano T et al., "Highly efficient gene transfer into primate embryonic stem cell with a simian lentivirus vector", Molecular Therapy, Aug. 2002, pp. 162-167, vol. 6, No. 2, San Diego, CA, US.
Bednarik et al., "Inactivation of the HIV LTR by DNA CpG methylation: evidence for a role in latency", EMBO Journal, 1990, pp. 1157-1164, vol. 9, No. 4, Oxford University Press.
Bednarik et al., "Methylation as a Modulator of Expression of Human Immunodeficiency Virus", Journal of Virology, Apr. 1987, pp. 1253-1257, vol. 61, No. 4, American Society for Microbiology.
Blomer U et al., "Highly Efficient and sustained gene transfer in adult neurons with a lentivirus vector", Journal of Virology, Sep. 1997, vol. 71, No. 9, US.
Bosselman R A et al., "Germline transmission of exogenous genes in the chicken", Science, Jan. 27, 1989, pp. 533-535, vol. 243, No. 4890.
Briskin M J et al., "Heritable retroviral transgenes are highly expressed in chickens", Proceedings of the National Academy of Sciences of the United States of America, pp. 1736-1740, vol. 88, No. 5.
U.S. Appl. No. 11/683,962, filed Mar. 8, 2007, Lois-Caballe et al.
U.S. Appl. No. 11/689,407, filed Mar. 21, 2007, Qin et al.
Burns et al., "Vesicular stomatitis virus G glycoprotein pseudotyped retroviral vectors: Concentration to very high titer and efficient gene transfer into mammalian and nonmammalian cells," *Proc. Natl. Acad. Sci. USA*, vol. 90, Sep. 1993, pp. 8033-8037.
Cameron E R, "Recent Advances in Transgenic Technology," Molecular Biotechnology, 1997, vol. 7: 253-265.
Chan A W S et al. "Transgenic Monkeys Produced by Retroviral Gene Transfer Into Mature Oocytes" Science, Jan. 12, 2001, vol. 291.
Chan A W S et al., "Transgenic cattle produced by reverse-transcribed gene transfer in oocytes," Proc. Natl. Acad. Sci USA, Nov. 1998, vol. 95, pp. 14028-14033.
Chan, "Transgenic Animals: Current and Alternative Strategies," Cloning, 1999, 1(1):25-46.
Chapman, Susan C et al., "Ubiquitous GFP expression in transgenic chickens using a lentiviral vector", Mar. 2005, pp. 935-940, vol. 132, No. 5, Cambridge, MA.

(Continued)

*Primary Examiner* — Michael Wilson
(74) *Attorney, Agent, or Firm* — Knobbe Martens Olson & Bear LLP

(57) ABSTRACT

The present invention relates to methods for producing transgenic animals, particularly transgenic rats, using retroviral constructs engineered to carry the transgene(s) of interest.

35 Claims, 22 Drawing Sheets
(14 of 22 Drawing Sheet(s) Filed in Color)

(56) References Cited

OTHER PUBLICATIONS

Charreau, Betrice et al., "Transgenesis in rats: Technical aspects and models", Transgenic Research, pp. 223-234, vol. 5, No. 4.
Chiochetti et al. (Biochim. Biophys. Acta (1352(2): 1930-202, 1997).
Cowan P J et al., "Targeting gene expression to endothelium in transgenic animals: a comparison of the human ICAM-2, PECAM-1 and endoglin promoters," Xenotransplantation, 2001, 10:223-231.
Dann, Christina Tenenhaus, "New technology for an old favorite: lentiviral transgenesis and RNAi in rats" Transgenic Res, 2007, 16(5): 571-580.
Deglon et al. (Hum. Gene Therapy 1(1): 179-190, 2000).
Dougherty, "Retrovirus Vectors for Efficient Transfer of Exogenous Genes into Target Cell Genomes", Biotechnology Trends Pharmaceutical Technology, Apr. 1990.
Duff, K et al., "Increased amyloid-β42(43) in brains of mice expressing mutant presenilin 1," Nature, Oct. 24, 1996, vol. 383.
Federspiel et al., 1996, PNAS, USA, 4931-4936.
Gage F H, "Cell Therapy," Nature, Apr. 30, 1998, vol. 392, p. 18-24.
Gerlai R "Gene-targeting studies of mammalian behavior: is it the mutation or the background genotype?" Trends Neurosci. 1996, 19, 177-181.
Gordon et al., "Integration and Stable Germ Line Transmission of Genes Injected Into Mouse Pronuclei," *Science*, vol. 214, Dec. 11, 1981, pp. 1244-1246.
Gray et al., "Radial arrangement of clonally related cells in the chicken optic tectum: Lineage analysis with a recombinant retrovirus" Proc. Natl. Acad. Sci. USA, vol. 83, pp. 7356-7360, Oct. 1988, Neurobiology.
Gropp M et al., "Stable genetic modification of human embryonic stem cells by lentiviral vectors", Molecular Therapy, Feb. 2003, pp. 281-287, vol. 7, No. 2, San Diego, CA, US.
Hamaguchi I et al., "Lentivirus vector gene expression during es cell-derived hematopoietic development in vitro", Journal of Virology, Nov. 2000, pp. 10778-10784, vol. 74, No. 22, US.
Hammer R E et al., "Spontaneous Inflammatory Disease in Transgenic Rats Expressing HLA-B27 and Human β$_2$m: An Animal Model of HLA-B27-Associated Human Disorders," Cell, Nov. 30, 1990, vol. 63, 1099-1112.
Haskel R E et al., "Efficient production of transgenic cattle by retroviral infection of early embryos", Lisss, Mar. 1995, pp. 386-390, vol. 40, No. 3, New York, NY.
Hoffman et al., "Rapid retroviral delivery of tetracycline-inducible genes in a single autoregulatory cassette" Proc. Natl. Acad. Sci; vol. 93; pp. 5185-5190, May 1996.
Ioannou, The Promise of Gene Therapy [online] 2001 [retrieved on Apr. 14, 2006]. Retrieved from the Internet: <URL: http://www.bath.ac.uk/bio-sci/hejmadi/gene%20therapy%20rev%2020els.pdf>.
ISI Web of Knowledge, www.isiknowledge.com, accessed Aug. 28, 2007 citing Lois et al., 2002, Science 295 (5556): 868-872.
Ivarie (TIBS 23(1): 14-19, 2003).
Jaenisch, "Germ line integration and Mendelian transmission of the exogenous Moloney leukemia virus," *Proc. Nat. Acad. Sci. USA*, vol. 73, No. 4, Apr. 1976, pp. 1260-1264.
Jahner D et al., "De novo methylation and expression of retroviral genomes during mouse embryogenesis", Nature, Aug. 12, 1982, pp. 623-628, vol. 298, No. 5875.
Kwon et al., (Biochem. Biophys. Res. Comm. 320:442-448, 2004).
Lam and Breakefield, 2000, J. Gene Med. 2:395-408.
Lever A M L et al., "Gene Therapy: from Bench to Bedside," Biochemical Society, 1999, vol. 27, No. 6, p. 841-847, University of Cambridge Department of Medicine, United Kingdom.
Lijnen H R et al., "α$_2$-Antiplasmin Gene Deficiency in Mice is Associated with Enhanced Fibrinolytic Potential Without Overt Bleeding," Blood, Apr. 1, 1999, vol. 93, No. 7, pp. 2274-2281.
Logan et al., 2002, Current Opinion in Biotechnology, 13:429-436.
Lois, Carlos et al., "Germline transmission and tissue-specific expression of transgene delivered by lentiviral vectors", Science, Feb. 1, 2002, pp. 868-872, vol. 295, No. 5556.

McGrew et al., "Efficient production of germline transgenic chickens using lentiviral vectors", European Molecular Biology Organization, 2004, pp. 728-733, vol. 5, No. 7.
Mench J A, "Ethics, Animal Welfare and Transgenic Farm Animals," CAB International, 1999.
Mitta B et al., "Advanced modular self-inactivating lentiviral expression vectors for multigene interventions in mammalian cells and in vivo transduction", Nucleic Acids Research, 2002, pp. 1-18, vol. 30, No. 21, Surrey, GB.
Miyoshi et al., "Development of a Self-Inactivating Lentivirus Vector," *Journal of Virology*, vol. 72, No. 10, Oct. 1998, pp. 8150-8157.
Mizuarai S et al., "Production of transgenic quails with high frequency of germ-line transmission using VSV-G pseudotyped retroviral vector", Biochemical and Biophysical Research Communications, Aug. 2001, pp. 456-463, vol. 286, No. 3, San Diego, CA, US.
Moreadith R W et al., "Gene targeting in embryonic stem cells: the new physiology and metabolism," J Mol Med, 1997, 75:208-216.
Muller, "Intracellular, genetic or congenital immunization—transgenic approaches to increase disease resistance of farm animals", Journal of Biotechnology, 1996, pp. 233-242, vol. 44, Vienna, Austria.
Naldini et al., "Efficient transfer, integration, and sustained long-term expression of the transgene in adult rat brains injected with a lentiviral vector", Proceedings of the National Academy of Sciences of USA, Oct. 15, 1996, pp. 11382-11388, vol. 93, No. 21, Washington US.
Naldini et al., "In Vivo Gene Delivery and Stable Transduction of Nondividing Cells by a Lentiviral Vector," *Science*, vol. 272, Apr. 12, 1996, pp. 263-267.
Osbourne et al., "Relief of transcriptional silencing in LCT-beta-globin retroviral vectors assayed in transgenic mice", 41$^{st}$ Meeting of the American Society of Hematology, New Blood, Nov. 1999, vol. 94, No. 10, pp. 177a.
Pain B et al., "Chicken embryonic stem cells and transgenic strategies", Cells Tissues Organs, 1999, pp. 212-219, vol. 165, Basel, Chicago.
Patten et al., 1997, Current Opinion in Biotechnology, 8:724-733.
Petitte J N et al., "The origin of the avian germ line and transgenesis in birds", Poultry Science, Aug. 1997, pp. 1084-1092, vol. 76, No. 8, Champaign, IL.
Pfeifer A et al., "Transgenesis by lentiviral vectors: Lack of gene silencing in mammalian embryonic stem cells and preimplantation embryos", Proceeding of the National Academy of Sciences of USA, Feb. 19, 2002, pp. 2140-2145, vol. 99, No. 4, Washington, US.
Pfeifer, 2004, Transgenic Research, 13:513-522.
Platt J L, "New directions for organ transplantation" Nature, Apr. 30, 1998, vol. 392.
Poeschia et al., "Efficient transduction of nondividing human cells by immunodeficiency virus lentiviral vectors," *Nature Medicine*, vol. 4, No. 3, Mar. 1998, pp. 354-357.
Powell et al., "Breeding of retroviruses by DNA shuffling for improved stability and processing yields," *Nature Biotechnology*, vol. 18, Dec. 2000, pp. 1279-1282.
Racay, 2002 Bratisl Lek Listy, 103:121-126.
Ramezani A et al., "Lentiviral Vectors for Enhanced Gene Expression in Human Hematopoietic Cells," Molecular Therapy, Nov. 2000, vol. 2, No. 5.
Reddy et al., "Expression of Rous Sarcoma virus-derived retroviral vectors in the avian blastoderm: Potential as stable genetic markers" Proc. Natl. Acad. Sci. USA vol. 88, pp. 30505-10509, Dec. 1991, Developmental Biology.
Reik et al., 1985, PNAS, USA, 82:1141-1145.
Ritchie et al., "Transgenic embryos and mice produced from low titre lentiviral vectors" Transgenic Res DOI 10.1007/s11248-007-9102-2.
Rubenstein et al., "Introduction of genes into preimplantation mouse embryos by use of a defective recombinant retrovirus" Proc. Natl. Acad. Sci. USA, vol. 83, pp. 366-368, Jan. 1986.
Sang, Helen "Prospects for transgenesis in the chick", Mechanisms of Development, Sep. 2004, pp. 1179-1186, vol. 121, No. 9.
Scott et al., "Generation of tissue-specific transgenic birds with lentiviral vectors", PNAS, Nov. 8, 2005, pp. 16443-16447, vol. 102, No. 45.

(56) References Cited

OTHER PUBLICATIONS

Shuman, R.M. "Production of transgenic birds", Experientia, 1991, p. 902-905, vol. 47, Switzerland.
Sirven A et al., "The human immunodeficiency virus type-1 central DNA flap is a crucial determinant for lentiviral vector nuclear import and gene transduction of human hematopoietic stem cells", Blood, Dec. 15, 2000, pp. 4103-4110, vol. 96, No. 13, Orlando, FL.
Smits et al., "Rat genetics: the next episode" Trends in Genetics vol. 22, pp. 232-240, No. 4 Apr. 2006.
Solaiman et al., "Modular retro-vectors for transgenic and therapeutic use", Molecular Reproduction and Development, Jun. 2000, pp. 309-315.
Soriano et al., "Retroviruses as Probes for Mammalian Development: Allocation of Cells to the Somatic and Germ Cell Lineages", Whitehead Institute for Biomedical Research, Jul. 4, 1986, pp. 19-29, vol. 46.
Stover M L et al., "Bone-directed expression of Col1a1 promoter-driven self-inactivating retroviral vector in bone marrow cells and transgenic mice", Molecular Therapy, Apr. 2001, pp. 543-550, vol. 3, No. 4, San Diego, CA, US.
Sukonnik et al., "Retrovirus vectors are rapidly silenced in de novo methylase knockout stem cells", $42^{nd}$ Meeting of the American Society of Hematology, San Francisco, Nov. 2000, vol. 96, No. 11, Part 1, pp. 429a.
Thoraval et al., "Germline transmission of exogenous genes in chickens using helper-free ecotropic avian leukosis virus-based vectors", Transgenic Research, Nov. 1995, pp. 369-377, vol. 4, No. 6, London.
Tsukui et al., 1995, Molecular Reproduction and Development 42:291-297.
Van Den Brandt et al., "Lentivirally Generated eGFP-Transgenic Rats Allow Efficient Cell Tracking In Vivo", 2004 Wiley-Liss, Inc. Genesis 39:94-99(2004).
Van Der Putten H et al., "Efficient insertion of genes into the mouse germ line via retroviral vectors" Proc. Natl. Acad. Sci USA, Sep. 1985, vol. 82, pp. 6148-6152.
Vargas, J. Jr et al., Novel integrase-defective lentiviral episomal vectors for gene transfer, Hum Gene Ther. Apr. 2004, 15(4):361-72.
Vigna et al., "Lentiviral vectors: excellent tools for experimental gene transfer and promising candidates for gene therapy," *The Journal of Gene Medicine*, vol. 2, 2000, pp. 308-316.
Wall et al., "Making Transgenic Livestock: Genetic Engineering on a Large Scale," *Journal of Cellular Biochemistry*, vol. 49, 1992, pp. 113-120.
Wolfgang et al., "Rhesus monkey placental transgene expression after lentiviral gene transfer into preimplantation embryos," PNAS, vol. 98, No. 19, Sep. 11, 2001, pp. 10728-10732.
Yang et al., "Long-term in vivo provision of antigen-specific T cell immunity by programming hematopoietic stem cells", PNAS, Mar. 22, 2005, pp. 4518-4523, vol. 102, No. 12.
Yee et al., "A general method for the generation of high-titer, pantropic retroviral vectors: Highly efficient infection of primary hepatocytes," *Proc. Natl. Acad. Sci. USA*, Vo. 91, Sep. 1994, pp. 9564-9568.
Yee et al., "Generation of High-Titer Pseudotyped Retroviral Vectors with Very Broad Host Range," *Method in Cell Biology*, vol. 43, Chapter 5, 1994, pp. 99-112.
Zajchowski L D et al., "Transgenic chickens: past, present, and future", Poultry and Avian Biology Reviews, 2000, pp. 63-80, vol. 11, No. 2, Northwood, GB.
Zennou V et al., "HIV-1 genome nuclear import is mediated by a central DNA flap", Cell Press, Apr. 14, 2000, pp. 173-185, vol. 101, No. 2, Cambridge, NA, US.
Zufferey et al., "Multiply attenuated lentiviral vector achieves efficient genes delivery in vivo," *Nature Biotechnology*, vol. 15, Sep. 1997, pp. 981-875.
Zufferey R et al., "Woodchuck hepatitis virus posttranscriptional regulartory element enhances expression of transgenes delivered by retroviral vectors", Journal of Virology, 1999, pp. 2886-2892, vol. 73, No. 4.
Zufferey, "Self-Inactivating Lentivirus Vector for Safe and Efficient In Vivo Gene Delivery", Journal of Virology, Dec. 1998, pp. 9873-9880, vol. 72, No. 12, Geneva Medical School, Switzerland and Cell Genesys, Foster City, California USA.
Skynner MJ et al., "Transgenic mice ubiquitously expressing human placental alkaline phosphatase (PLAP): an additional reporter gene for use in tandem with beta-galactosidase (IacZ)", *Int J Dev Biol*, Jan. 1999, 43(1):85-90.
Lu JK et al., "Production of transgenic dwarf surfclams, *Mulinia lateralis*, with pantropic retroviral vectors", *Proc Natl Acad Sci USA*, Apr. 16, 1996, 93(8):3482-6.
International Search Report for PCT Application PCT/US02/29130 dated Jun. 27, 2003.
International Search Report for PCT Application PCT/US02/29157 dated Sep. 16, 2003.
Cheng et al. (1995) Activation of the myogenin promoter during mouse embryogenesis in the absence of positive autoregulation. Proc. Natl. Acad. Sci. 92:561-565.
Schmidt et al. (1990) The cytomegalovirus enhancer: a pan-active control element in transgenic mice. Molecular and Cellular Biology. p. 4406-4411.
U.S. Appl. No. 12/795,581, filed Jun. 2, 2010, Lois-Caballe et al.
U.S. Appl. No. 12/769,157, filed Apr. 28, 2010, Lois-Caballe et al.

* cited by examiner

5x

20x

GFP (SEQ ID NO:3)

atggtgagcaagggcgaggagctgttcaccggggtggtgcccatcctggtcgagctggacggcgacgtgaacggccacaag
ttcagcgtgtccggcgagggcgagggcgatgccacctacggcaagctgaccctgaagttcatctgcaccaccggcaagctgc
ccgtgcccctggcccaccctcgtgaccaccttcacctacggcgtgcagtgcttcagccgctaccccgaccacatgaagcagcac
gacttcttcaagtccgccatgcccgaaggctacgtccaggagcgcaccatcttcttcaaggacgacggcaactacaagaccg
cgccgaggtgaagttcgagggcgacaccctggtgaaccgcatcgagctgaagggcatcgacttcaaggaggacggcaacat
cctggggcacaagctggagtacaactacaacagccacaacgtctatatcatggccgacaagcagaagaacggcatcaaggtg
aacttcaagatccgccacaacatcgaggacggcagcgtgcagctcgccgaccactaccagcagaacacccccatcggcgac
ggccccgtgctgctgcccgacaaccactacctgagcacccagtccgccctgagcaaagaccccaacgagaagcgcgatcac
atggtcctgctggagttcgtgaccgccgccgggatcactctcggcatggacgagctgtacaagtaa

FIG. 16

H2B-GFP  (SEQ ID NO:5)

accatgccagagccagcgaagtctgtccgcccgaaaaagggctccaagaaggcggtgactaaggcgcagaagaaagg
cggcaagaagcgcaagcgcagccgcaaggagagcgtattccatctatgtgaagcaggttctgaagcaggtccacccgacaccg
gcatttcgtccaaggccatgggcatcatgaattcgttttgtgaacgacatttttcgacgcagtgagcttcccgcctgcg
cattacaacaagcgtcgaccatcaactccaggagatccaggaggcgctgcctgctgcctgggagttggccaagc
acgccgtgtccgagggtactaaggccatcaccagccaccagtcgaggatcacaccggtcgccaccaagttcagcgtgtccggc
cgaggagctgttcaccggggtgttgccacctacggcgccgatcgcccaccagctgaaacgcgacgtaaacgccaccagcaagctgcccgtgccctgccca
gagggcgagggcgatgccaccctacgggtccaggagcgcgactcggcgtgcaggagcgacgacgactccgagcgactcttcaagtccg
ccctcgtgaccaccctgacctacggtccaggagcgcaccatcttcaaggacgacggcaactacaagacccgcgccgaggtgaagtt
ccatgcccgaaggctaccgtccaggagcgcatcgagctgaaggcaccatcgagctgaaagggcatcgagctgaaaggcaatctcaaggtggccaacatcctgggccacaagct
cgagggcgacacctgtgaaccgcatacagcagcagaagaacccatcgccgacaagcagaagaacggcatcaaggtgaacttcaagatccgcc
ggagtacaactacaacagccacaacgtctatatcatgccgacaagcagaagaatgggaatcaaggtcaaggtgaacttcaagatccgcc
acaacattgagggcgacggcgtgcagctcgccgaccactaccagcagaacacccccatcggcgacggccccgtgctgc
ccgacaaccactacctgagcacctgctgagcacctaccagtccgccctgagcaaagaccccaacgagaagcgcgatcacatggtcctgctgagtt
cgtgaccgccgccggtattcactctgagcatgaaccgagagctgtacaagtaa

FIG. 17

HIV NL4.3 flap (SEQ ID NO:1)

acaaatggcagtattcatccacaattttaaaagaaaaggggggattggggggtacagtgcaggggaaagaatagtagacataat
agcacagacatacaaactaaagaattacaaaaacaaattacaaaaattcaaaattttcgggtttattacagggacagcagagatc
cagtttgg

FIG. 18A

WRE (SEQ ID NO:4)

atcgataatcaacctctggattacaaaatttgtgaaagattgactggtattcttaactatgtgtctcctttacgctatgtggatatacgctg
ctttaatgcctttgtatcatgctattgcttcccgtatgctgtgtgcactgtgtttgctgacgcaacccccactggttcaacaatctgttataaatctggttgctgtctcttatgaggagttg
tgcccgttgtcaggcaacgtggcgtggtgtgcactgtttccccctattgccaacggactcatcgccgccttcccgcctggcctggcatttgccactgactacgtccttcgtatttgtgcgggaagctgacgtccttcccgctgcccgctgctccacgctg
agctccttccggactttcgctttccccctattgccacggcctgccgcctggcctggcatttgccactgactacgtccttcgtatttgtgcgggaagctgacgtccttcccgctgcccgctgctccacgctg
ctggctgttgggcactgacaattccgtggtgttgtgcgggaccctcggcctcactcaatccagcgacctcctccagcgacctcctccgagcgaccttcctccgagacttcctccgacgctgctccacctg
gattctgccgcggacgtcttcgccttcgccttcgcccttcgcgcctttcgcgcctcttccggaccttcctccttgggccgccttcctccgcgcctcccgctgctccggctctgc
ggcctcttccgcgtcttccgcttcgcgccttcgcgcctttcgcgcctcttccgaccttccttggccgccctcccgctcccccgctgatcgat

FIG. 18B

MYOGENIN PROMOTER   (SEQ ID NO:7)

gtctctagctgcatatgtagcagaagatggcctagtcggccatcattgggaagagaggcccccttggtattgcaaactatatgcccc
agtacaggggaacgccaggccaagaagtgggaatgagtgggtagggagcaggcaggcgggggaggggggttagggaa
cttttgggatagcatttgaaatgtaaatgaagaaaatatctaataaaaataattaaaaaagagcgtcagacaggggactgaaca
gctcttgactagggagagaaggcaatgtagagtagtcttgttctaatccttgctaaacactgacttcacctgaccctacta
cttaaggcccccccccttacttaagaagtccctgtgttctcttacttcaatctacccccaacatcatgagacctggtcaaagaagctg
tagaaacccaaaagttgaatccatttgccctctgggtttctgtctttgcctcgatgtagtggtaggtctttagggtctcatggactgac
acacacacacacacgcccaaatctggagtggtcctgatgtgtagtggtaggtctttagggtctcatggactgac
atagtatgttttaaggtgctgctgagcaggaaagaaggctaagtggatttcaagaccccttccgtccgtccaagacaaccc
ctttcttgttccctttcctgcctgtccacccagctgccttggaccatggagagagaagtaggcaggagccccgggtaggagtaatt
gaaaggagcagatgagacggggggaaatgcacccaccccaccttcccctgcccacagggggctgtggagaaatgaaaactaat
caaattacagcgcgacgcctcccgacccgtgcacagggaccgcgcctgggcaggagccgcctgcagggtgggtggggg
caaaggagaggaaggggaatcacatgtaaccactgaaaacgtcttgatgtgcagcaacagcttagagggggctcaggttt
ctgtgccgttgctatattatctctggttcatgccagcaggaggggttttaaatggcacccagcagttggtgtgaggggctgcgg
gagcttgggggccagtggccaggaacaagcctttttgcgacctgatg

FIG. 19A

Lck promoter (partial)    (SEQ ID NO:6)

tgagtcaccatgtgattgctgggaattgaactcaagacctctggaagagagcagtcagtgctctttttgtttgtttgtttgtttgtttgg
gtttttttttgagacagggtttctctgtgtagccctgtgtgggtagccctgtgtgtgagtgtgtgtgtttgtggtatgttgc
aaatagattaaacaactgagagatgaataggtcttgacatcaaaaacatgctgaacccttattaatctaacactcag
agacaggagcatctgcaggtttgaggccagctagctctacagaatgaattcaggtcaagtcagcttgtctacaaagtga
gtttcagatctcaaggccagcagccgataattgaggaccagtgctcaggaggaggcacacggaattccagaggctacagaggagcctcgct
cgcttggcaaaccgattagagcaactctactttactgctgtgtctatgaggttctgcttgatttcatttgacaaaaagtttccacagctaaacca
ctgacctggttagagcaactctactttactgctgtgtctatgaggttctgcttgatttcatttgacaaaaagtttccacagctaaacca
gcaagggagccgaagtagacacagcccaccgggccgccccaacaggtttctctgctgctgagctgaggttgactcta
gaagaaactctgaagagagactgtttgagtgtggggtaggggtaggggtgctggggttggggagagagagagagagagagagagggt
ggagctggaacctctcagcttcggttgcccccagaacttggcaaagtgtgtgatgtctcccaggtagtcccccaaggaggaggctagca
ggaatgaaactctcggtttcccccagaacttggcaaagtgtgtgatgtctcccaggtagtcccccaaggaggaggctagca
gagctggggaggcaggaagtgggggtaactaacaaagatgcctgctgtgcgttgccatccagtggaggatg
ggactagctttgggcctgggcccaatggggcctggggcctggggcctgtgaacttggtgctgagctcagagggaaccccagtcaggagcttgaatcccacgat
tcagcgcttctgtctgcgggcccaatggggcctgggcctggggctaggccagcttagggccagcttcagggccagcttcaggtagcttgggtgcttcaggtaactcctccattccttcaggatcatgggctgt
gtctgatgttggggcgagtggttaggcgagtggttaggcagcttagggccagcttcagggccagcttcaggaaacaggctctaggat
gtctgatgttggggcgagtggttaggcgagtggttaggcagcttagggccagctcttcaggaaacaggctctaggat

*FIG. 19B*

HUMAN UBIQUITIN PROMOTER (SEQ ID NO:2)

gggtgcagcggcctccgcgccgggttttggcgcctccgcctccgcggcgcccctcctcacggcgagcgctgccacgtcagacg
aagggcgaggacgcgttcctgatcccttccgcccgacgctcaggacagcgccgcgctgctcataagactcggcttagaacc
ccagtatcagcagaaggacatttaggacaggactggtgtgactctaggcacctgtttcttccagagagcggaacaggcga
ggaaaagtagtccctctcggcgattctgcgagggatctcgtgggagcggttcttgtttgtggatcgctgtgatcgtcacttggtgagttgcg
gtgtggcacagcagttccgtcgcgcagccggatttggggtcgcgcgtcttgttgtggatcgctgtgatcgtcacttggtgagttgcg
ggctgctgggctggccgggccggccttcgtgcgtcgccgcgacgttctgccttgggggttgggggagcgcacaaaatgccgctgttccgagtcttgaa
gtagtctgggtccgcgagcaaggttgccctgaactggtgagtcgttgaaacaaggtggggggtggggggcacaaaatgccgctgttccgagtcttgaa
tggaagacgcttgtaaggcgggaaagctcttatcggtgagtcgttgaaacaaggtgggggtgggggcacaaaatgccgctgttccgagtcttgaa
ggccttcgctaatgcggaaagctcttatcggtgagtcgttgaaacaaggtggctgggacccctgcacccgtaagtttgtcactg
actggagaactcggtttcgtcgtgacgtcacccgttcgttggcttgcttatataatgcagggtctctgaatgcgacaggccctgggagctggggac
gcgcgcctcgtcgtgtcgcagacgcaggttcacccgttcgttggcctaggggggttcggcctaggtgggccacctgccggtaggtgtcggtagg
ctttctccgtcgcagaactcggtttctgtcgcagacgcaggttcacccgttcgttggcctaggtgggccacctgccggtaggtgtcggtagg
ggataagtgaggtgttcagttctttgaagttttttggcttcagttgctttgggtcgcagacgcaggttgaatcatccgttggcctaggtggggag
gttggcgagtgtgttgtttgaagttttttggcttcagttgctttgggtcgcagcgcaggttgaatcatccgttggctaggtggggag
gtccgctaaattctggccgttttttggcttttttgttagaca

FIG. 20

HIV-1 FLAP + UBIQUTIN + GFP + WRE    (SEQ ID NO:8)

ctgcagacaaatgcagtattcatcccacatttttaaagaaaaggggggattgggggggtacagtgcagtgcaggggaaagaatagtag
acataatagcaacagacatacaaactaaagaattacaaaaacaaattacaaaaatttcaaaatttcggtttattaccgggacagc
agagatccagtttggctgcagttaattaaagatctggttcagcgccgccggtttggcgctccggcgacgacccc
cctcctcacggacgagcgctgccacgtcagacgaaggcgaggagcgttcctgatccttccgcccgacgctcaggacagc
ggcccgctgctcataagactcggccttcagtcagacaagagaaagtagtccttcggcgattctgcggaggatccgtgggcg
actggtttcttccagagagcgagacaggcggaacaggcggaaggagaaagtagtccttcggcgattcgcgaggatccgtgggcg
tgaacgccgatgattatataaggacgcgccgggtgtggcacacgtagttccgtgccggccgaggctttgggtcgcggttcttgttt
gtggatcgtgtgatcgtcacttggtgagtcgtcacttggtgagtcgtgagccgcccgctcgtggg
acggagcgtgtggagagaccgccaaggcgcgccaaggcgtagttgatcatggcctgagcgacaaggtgccctgaactggggttggggggag
cgcacaaaatgcggctgttccgagttcttgaatgaagacgctgtaagggggctgtgaggctgttgaaacaaggtggggg
gcatgtgggcggaacccaaggtcttgaggcttcgctaatgccgggaaagctcttattcggtgagatggcctggggca
ccatctgggaccctgacgtgaagtttgtcactgactgagccgcgccctcgtgtgtcgtgactcaccgttctgttgctcacctttgttgct
gccgttgggcagtgccgtgccggtagtgctggggagcgcggagcttccggggagtcgtgcgcgcaagacgcaggttcttggtctgtcgtaatgcagg
gtgggccacctgccggtcgccggagacctgttgtgagagcagtgaggatagtgagcgtgttttgtgaagtttttgagcactttgaagtgtaatcattgg
tcacagggccgccggagacctgttgtgagagcagtgaggatagtgagcgtgttttgtgaagtttttgcctttgttttggtctgtcgtaatgtagta
gctgaagctcggttgctaatatgctcgctagtagtcgctaaattcgctaaatttctgccctaaattctgaccgtttttgacttttgacaagctctgcaggtc
gtcaatatgtattttcagtgttagactagtagtcgctaaattcgccgctaaatttctgccgtaaattctgcaccgggtggtgccatctggtcgagc
gactctagaggatcccccggggtaccatgcagttcagcgtgccgcaaggtccggcgaggaggcgagggcgatgccaccctacgcaagctgaccctga
tggacggcgactgaacggcacacaggcaaagtgccgtgccgtcctgcccacttcagctccacctacggcgtgcagtgcttcagc
agttcatctgcaccacccggcaagctgcccgtgccgtggaccaccttcagctgcaccacctcggcggcccacctcagctgcactcttca
gctacccgaccacatgaagcagcacgacttcttcaagtccgcgaggcaccggcctacgtccaggagcgcaccatcttcttca
aggacgacggcaactacaagacccgcgccgaggtgaagttcgaggtgccgacacccgtgaaccgcatggagctgaaggc
atcgacttcaaggaggacggcaacatctggggcacatctggtgaataacagccacaatgatccgcctatatcctgaccga
caagcagaagaacggcatcaaggcacttcaagatcggcacacaacactcgaggacggcagcgtgcagctcgccgaccacta
ccagcagaacaccccatcggcgacggccccgtgctgctgcccgacaacaccactacgagaaaccagctcctgagcaa
agcccccaacgagaagcgcgatcacatgggcatgatggggccgccacgagctgtacaagtaggcggccgccgcatcacgcgagctg
tacaagtaaggccgccgctccgatcatctccttttacctagtagataacgccttaatgcctttaatgcctgataaacctgtgaaagatt
gactggtattctcctcctgtataaatcctggttctctctttgttctgtaataatgcctgggcagtgtgagctgggcgtggtgtcactgt
cattttctgcaccctctggtctctctctggttggcattggacttctcggccttgagctcgcccatggccttccccctattgcc
acggcggacggacctttggggtcggggaacttgttggcactgagtgggcgggccgtgttgtgctccttccc
ggaagctgacgtcttccatggccgcgtgtggcgcctgtctgccgctgtgtccgcgctctgcggcctcttccgcgtctcttcgctacgtccttcgc
cctcaatccagcggaccttccttcccgcgctctctgccgctgtgctcgccgcgctcgccgctctcgccgctcttcgccttcgccctccgagatcgatcgatcgatgtgaccctgagggtacc
ggatctccctttgggccgcctccccgcctgggacgccttccttcccgcgctctctgccgctgtgctcgccgctcgccgctctcgccgctcttcgccttcgccctccgagacgatcgatcgatgtgaccctgagggtacc

```
                            SEQUENCE LISTING

<160> NUMBER OF SEQ ID NOS: 9

<210> SEQ ID NO 1
<211> LENGTH: 178
<212> TYPE: DNA
<213> ORGANISM: Human immunodeficiency virus

<400> SEQUENCE: 1
acaaatggca gtattcatcc acaattttaa aagaaaaggg gggattgggg ggtacagtgc     60
aggggaaaga atagtagaca taatagcaac agacatacaa actaaagaat tacaaaaaca    120
aattacaaaa attcaaaatt ttcgggttta ttacagggac agcagagatc cagtttgg     178

<210> SEQ ID NO 2
<211> LENGTH: 1221
<212> TYPE: DNA
<213> ORGANISM: Homo sapiens

<400> SEQUENCE: 2
gggtgcagcg gcctccgcgc cgggttttgg cgcctcccgc gggcgccccc ctcctcacgg     60
cgagcgctgc cacgtcagac gaaggggcgca ggagcgttcc tgatccttcc gcccggacgc    120
tcaggacagc ggcccgctgc tcataagact cggccttaga accccagtat cagcagaagg    180
acattttagg acgggacttg ggtgactcta gggcactggt tttctttcca gagagcggaa    240
caggcgagga aaagtagtcc cttctcggcg attctgcgga gggatctccg tggggcggtg    300
aacgccgatg attatataag gacgcgccgg gtgtggcaca gctagttccg tcgcagccgg    360
gatttgggtc gcggttcttg tttgtggatc gctgtgatcg tcacttggtg agttgcgggc    420
tgctgggctg gccggggctt tcgtggccgc cgggccgctc ggtgggacgg aagcgtgtgg    480
agagaccgcc aagggctgta gtctgggtcc gcgagcaagg ttgccctgaa ctggggggttg    540 gggggagcgc acaaaatggc ggctgttccc gagtcttgaa tggaagacgc ttgtaaggcg    600
```

```
ggctgtgagg tcgttgaaac aaggtggggg gcatggtggg cggcaagaac ccaaggtctt      660
gaggccttcg ctaatgcggg aaagctctta ttcgggtgag atgggctggg gcaccatctg      720
gggaccctga cgtgaagttt gtcactgact ggagaactcg ggtttgtcgt ctggttgcgg      780
gggcggcagt tatgcggtgc cgttgggcag tgcacccgta cctttgggag cgcgcgcctc      840
gtcgtgtcgt gacgtcaccc gttctgttgg cttataatgc agggtggggc cacctgccgg      900
taggtgtgcg gtaggctttt ctccgtcgca ggacgcaggg ttcgggccta gggtaggctc      960
tcctgaatcg acaggcgccg gacctctggt gaggggaggg ataagtgagg cgtcagtttc     1020
tttggtcggt tttatgtacc tatcttctta agtagctgaa gctccggttt tgaactatgc     1080
gctcggggtt ggcgagtgtg ttttgtgaag tttttaggc acctttgaa atgtaatcat       1140 ttgggtcaat atgtaatttt cagtgttaga ctagtaaatt gtccgctaaa ttctggccgt     1200
tttggctttt tttgttagac a                                                1221
```

<210> SEQ ID NO 3
<211> LENGTH: 720
<212> TYPE: DNA
<213> ORGANISM: Artificial Sequence
<220> FEATURE:
<223> OTHER INFORMATION: This sequence encodes for a green fluorescent
      protein variant.

<400> SEQUENCE: 3

```
atggtgagca agggcgagga gctgttcacc ggggtggtgc ccatcctggt cgagctggac       60
ggcgacgtga acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccttcaccta cggcgtgcag tgcttcagcc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actcacggca tggacgagct gtacaagtaa      720
```

<210> SEQ ID NO 4
<211> LENGTH: 604
<212> TYPE: DNA
<213> ORGANISM: Woodchuck hepatitis virus

<400> SEQUENCE: 4

```
atcgataatc aacctctgga ttacaaaatt tgtgaaagat tgactggtat tcttaactat       60
gttgctcctt ttacgctatg tggatacgct gctttaatgc ctttgtatca tgctattgct      120
tcccgtatgg ctttcatttt ctcctccttg tataaatcct ggttgctgtc tctttatgag      180
gagttgtggc ccgttgtcag caacgtggc gtggtgtgca ctgtgtttgc tgacgcaacc       240
cccactggtt ggggcattgc caccacctgt cagctccttt ccgggacttt cgctttcccc      300
ctccctattg ccacggcgga actcatcgcc gcctgccttg cccgctgctg acaggggct       360 cggctgttgg gcactgacaa ttccgtggtg ttgtcgggga agctgacgtc ctttccatgg      420
```

| | |
|---|---|
| ctgctcgcct gtgttgccac ctggattctg cgcgggacgt ccttctgcta cgtcccttcg | 480 |
| gccctcaatc cagcggacct tccttcccgc ggcctgctgc cggctctgcg gcctcttccg | 540 |
| cgtcttcgcc ttcgccctca gacgagtcgg atctcccttt gggccgcctc cccgcctgat | 600 |
| cgat | 604 |

<210> SEQ ID NO 5
<211> LENGTH: 1119
<212> TYPE: DNA
<213> ORGANISM: Artificial Sequence
<220> FEATURE:
<223> OTHER INFORMATION: This sequence encodes for a fusion protein between human histone 2B protein and a green fluorescent protein variant.

<400> SEQUENCE: 5

| | |
|---|---|
| accatgccag agccagcgaa gtctgctccc gccccgaaaa agggctccaa gaaggcggtg | 60 |
| actaaggcgc agaagaaagg cggcaagaag cgcaagcgca gccgcaagga gagctattcc | 120 |
| atctatgtgt acaaggttct gaagcaggtc caccctgaca ccggcatttc gtccaaggcc | 180 |
| atgggcatca tgaattcgtt tgtgaacgac attttcgagc gcatcgcagg tgaggcttcc | 240 |
| cgcctggcgc attacaacaa gcgctcgacc atcacctcca gggagatcca gacggccgtg | 300 |
| cgcctgctgc tgcctgggga gttggccaag cacgccgtgt ccgagggtac taaggccatc | 360 |
| accaagtaca ccagcgctaa ggatccaccg gtcgccacca tggtgagcaa gggcgaggag | 420 |
| ctgttcaccg gggtggtgcc catcctggtc gagctggacg gcgacgtaaa cggccacaag | 480 |
| ttcagcgtgt ccggcgaggg cgagggcgat gccacctacg gcaagctgac cctgaagttc | 540 |
| atctgcacca ccggcaagct gcccgtgccc tggcccaccc tcgtgaccac cctgacctac | 600 |
| ggcgtgcagt gcttcagccg ctaccccgac cacatgaagc agcacgactt cttcaagtcc | 660 |
| gccatgcccg aaggctacgt ccaggagcgc accatcttct tcaaggacga cggcaactac | 720 |
| aagacccgcg ccgaggtgaa gttcgagggc gacaccctgg tgaaccgcat cgagctgaag | 780 |
| ggcatcgact tcaaggagga cggcaacatc ctggggcaca gctggagta caactacaac | 840 |
| agccacaacg tctatatcat ggccgacaag cagaagaacg gcatcaaggt gaacttcaag | 900 |
| atccgccaca acatcgagga cggcagcgtg cagctcgccg accactacca gcagaacacc | 960 |
| cccatcggcg acggccccgt gctgctgccc gacaaccact acctgagcac ccagtccgcc | 1020 |
| ctgagcaaag accccaacga aaagcgcgat cacatggtcc tgctggagtt cgtgaccgcc | 1080 |
| gccgggatca ctctcggcat ggacgagctg tacaagtaa | 1119 |

<210> SEQ ID NO 6
<211> LENGTH: 1276
<212> TYPE: DNA
<213> ORGANISM: Murine

<400> SEQUENCE: 6

| | |
|---|---|
| tgagtcacca tgtgattgct gggaattgaa ctcaagacct ctggaagagc agtcagtgct | 60 |
| cttttttgttt gtttgtttgt tgtttgtttt gggttttttt tttgagacag ggtttctctg | 120 |
| tgtagccgtg tgtgtggggt agccctgtgt gtgagtgtgt gtgtgtgtgt ttgtggtatg | 180 |
| ttgcaaaata gattaaacaa ctgagagatg gaataggtct tcttgacatc aaaaacatga | 240 |
| tcgtgaaccc ctttattaaa tctaacactc agagacagga gcatctctgc aggtttgagg | 300 |
| ccagcctgct ctacagaatg aatttcaggt ctcaaggtca gcttggtcta caaagtgagt | 360 |
| ttcagatctc aaggccagcc aagactatgc agtaagacct tagctaaaat aaataaataa | 420 |

```
ataaaataaa ataaaagtta atcttcgctt ggcaaaccga taattgagga ccagtgctca      480
ggaaggaggc acacgggaat tccagaggct acagagggag cctcgctctg acctggttag      540
agcaactcta ctttactggc tgtgtctatg aggttctgct tgatttcatt tgacaaaaag      600
tttccacagc taaaccaggc aagggagccg aagtagacac agccacccgg ccgcgccca       660 acaggtttct ctctgctgct gagaagcaaa agcctgtttg aagaaactct ctgaaggaga      720
ctgtggttga gtggtggggg taggggtgct ggggttgggc tgaggctgag ggttgactct      780
aaggagctgg aacctctcag cttcggtggc taggcagggg agttgtaatg aagagggaca      840
ggtaccctcc ttggtggagg agggtggaat gaaactctcg gtttccccca gaacttggca      900
aagtgtgtgt gatgtctccc aggtagtccc ccaaggagg aggctagcag agctggggag       960
gcaggaagtg ggtaactaga ctaacaaaga tgcctgcctg tggcggtttg cccatcccag     1020
gtgggagggt gggactagcc ttgggcctgg gcctcctgtg aacttggtgc ttgagggctc     1080
agagggaacc cagtcaggag cttgaatccc acgattcagc gcttctgtct gcggccaatg     1140
ggggcctctg agctgacgat ctcgggtact ttttgtaact tccagaacag ggctctagga     1200
tgtctgatgt tggggcgagt ggcttagggc cagctccttc aggcctctct acattccttc     1260
agggatcatg ggctgt                                                     1276

<210> SEQ ID NO 7
<211> LENGTH: 1140
<212> TYPE: DNA
<213> ORGANISM: Murine

<400> SEQUENCE: 7
gtctctagct gcatatgtag cagaagatgg cctagtcggc catcattggg aagagaggcc       60
ccttggtatt gcaaactata tgccccagta caggggaacg ccagggccaa gaagtgggaa      120
tgagtgggta ggggagcagg gcggggggag gggggttag ggaacttttg ggatagcatt       180
tgaaatgtaa atgaagaaaa tatctaataa aaaataattt aaaaagagc gtcagacagg       240 ggactgaaca gctcttgact agggggagaag aaggcaatgt agagtagtct gtgagttcta    300
atccttgcta aacactgact tcacctgacc cctactactt aaggcccccc ccttacttaa    360
agaagtccct gtgttctctt acttcaatct accccaaca tcatgagacc tggtcaaaga     420 agctgtaaa acccaaaagt tgaatccatt tgcccttctg ggtttctgtc tttgcctcca     480
tggacgatag ggacacacac acacacacac acacacacac acacacacac acgccccaaa    540
tctggagtgg tcctgatgtg gtagtggtag gtctttaggg gtctcatggg actgacatag    600
tatggtttaa ggtgctgctg agcaggaaag agaaggctaa gtggatttc aagacccctt     660 cccgtccgtc caagacaacc cctttcttgt tcccttcctg ccctgtccac cagctgcctt    720
ggaccatgga ggagagagta ggcaggaggc ccgggtagga gtaattgaaa ggagcagatg    780 agacgggggga atgcacccac ccccaccttc cctgccccac aggggctgtg gagaaatgaa   840
aactaatcaa attacagccg acggcctccc gacccgtgca caggagccgc ctgggccagg    900
ggcaggcctg cagggtgggg tggggcaaa aggagaggga aggggaatca catgtaacca     960
ctggaaacgt cttgatgtgc agcaacagct tagagggggg ctcaggtttc tgtggcgttg   1020
gctatattta tctctgggtt catgccagca gggagggttt aaatggcacc cagcagttgg   1080
tgtgaggggc tgcgggagct tgggggccag tggcaggaac aagccttttg cgacctgatg   1140

<210> SEQ ID NO 8
```

<211> LENGTH: 2853
<212> TYPE: DNA
<213> ORGANISM: Artificial Sequence
<220> FEATURE:
<223> OTHER INFORMATION: This sequence represents a vector insert
comprising a human immunodeficiency virus
sequence, a green fluorescent protein variant
sequence, a human ubiquitin promoter sequence and
a woodchuck hepatitis regulator element sequence.

<400> SEQUENCE: 8

```
ctgcagacaa atggcagtat tcatccacaa ttttaaaaga aaagggggga ttggggggta      60
cagtgcaggg gaaagaatag tagacataat agcaacagac atacaaacta agaattaca     120
aaaacaaatt acaaaaattc aaaattttcg ggtttattac agggacagca gagatccagt    180
ttggctgcag ttaattaaag atctgggtgc agcggcctcc gcgccgggtt ttggcgcctc    240
ccgcgggcgc ccccctcctc acggcgagcg ctgccacgtc agacgaaggg cgcaggagcg    300
ttcctgatcc ttccgcccgg acgctcagga cagcggcccg ctgctcataa gactcggcct    360
tagaacccca gtatcagcag aaggacattt taggacggga cttgggtgac tctagggcac    420
tggttttctt tccagagagc ggaacaggcg aggaaaagta gtcccttctc ggcgattctg    480
cggagggatc tccgtggggc ggtgaacgcc gatgattata taaggacgcg ccgggtgtgg    540
cacagctagt tccgtcgcag ccgggatttg ggtcgcggtt cttgtttgtg gatcgctgtg    600
atcgtcactt ggtgagttgc gggctgctgg gctggccggg gctttcgtgg ccgccgggcc    660
gctcggtggg acggaagcgt gtggagagac cgccaagggc tgtagtctgg gtccgcgagc    720
aaggttgccc tgaactgggg gttggggggga gcgcacaaaa tggcggctgt tcccgagtct    780
tgaatggaag acgcttgtaa ggcgggctgt gaggtcgttg aaacaaggtg gggggcatgg    840
tgggcggcaa gaacccaagg tcttgaggcc ttcgctaatg cgggaaagct cttattcggg    900
tgagatgggc tggggcacca tctggggacc ctgacgtgaa gtttgtcact gactggagaa    960
ctcgggtttg tcgtctggtt gcgggggcgg cagttatgcg gtgccgttgg gcagtgcacc   1020
cgtacctttg ggagcgcgcg cctcgtcgtg tcgtgacgtc acccgttctg ttggcttata   1080
atgcagggtg gggccacctg ccggtaggtg tgcggtaggc ttttctccgt cgcaggacgc   1140
agggttcggg cctagggtag gctctcctga atcgacaggc gccggacctc tggtgagggg   1200
agggataagt gaggcgtcag tttctttggt cggttttatg tacctatctt cttaagtagc   1260
tgaagctccg gttttgaact atgcgctcgg ggttggcgag tgtgttttgt gaagtttttt   1320
aggcaccttt tgaaatgtaa tcatttgggt caatatgtaa ttttcagtgt tagactagta   1380
aattgtccgc taaattctgg ccgttttttgg ctttttttgtt agacaaagct tctgcaggtc   1440
gactctagag gatccccgg gggtaccatg gtgagcaagg gcgaggagct gttcaccggg   1500
gtggtgccca tcctggtcga gctggacggc gacgtgaacg gccacaagtt cagcgtgtcc   1560
ggcgagggcg agggcgatgc cacctacggc aagctgaccc tgaagttcat ctgcaccacc   1620
ggcaagctgc ccgtgccctg gcccaccctc gtgaccacct tcacctacgg cgtgcagtgc   1680
ttcagccgct accccgacca catgaagcag cacgacttct tcaagtccgc catgcccgaa   1740
ggctacgtcc aggagcgcac catcttcttc aaggacgacg gcaactacaa gacccgcgcc   1800
gaggtgaagt tcgagggcga caccctggtg aaccgcatcg agctgaaggg catcgacttc   1860
aaggaggacg gcaacatcct ggggcacaag ctggagtaca actacaacag ccacaacgtc   1920
tatatcatgg ccgacaagca gaagaacggc atcaaggtga acttcaagat ccgccacaac   1980
atcgaggacg gcagcgtgca gctcgccgac cactaccagc agaacacccc catcggcgac   2040
```

-continued

```
ggccccgtgc tgctgcccga caaccactac ctgagcaccc agtccgccct gagcaaagac    2100
cccaacgaga agcgcgatca catggtcctg ctggagttcg tgaccgccgc cgggatcact    2160
cacggcatgg acgagctgta caagtaagcg gccgctctag agaattcgat atcaagctta    2220
tcgatatcga taatcaacct ctggattaca aaatttgtga agattgact ggtattctta     2280 actatgttgc tccttttacg ctatgtggat acgctgcttt aatgcctttg tatcatgcta    2340
ttgcttcccg tatggctttc attttctcct ccttgtataa atcctggttg ctgtctcttt    2400
atgaggagtt gtggcccgtt gtcaggcaac gtggcgtggt gtgcactgtg tttgctgacg    2460 caaccccac tggttggggc attgccacca cctgtcagct cctttccggg actttcgctt     2520 tcccctccc tattgccacg gcggaactca tcgccgcctg ccttgcccgc tgctggacag     2580
gggctcggct gttgggcact gacaattccg tggtgttgtc ggggaagctg acgtcctttc    2640
catggctgct cgcctgtgtt gccacctgga ttctgcgcgg gacgtccttc tgctacgtcc    2700
cttcggccct caatccagcg gaccttcctt cccgcggcct gctgccggct ctgcggcctc    2760
ttccgcgtct tcgccttcgc cctcagacga gtcggatctc cctttgggcc gcctccccgc    2820
ctgatcgata tcgatgtcga cctcgagggt acc                                 2853
```

<210> SEQ ID NO 9
<211> LENGTH: 9941
<212> TYPE: DNA
<213> ORGANISM: Artificial Sequence
<220> FEATURE:
<223> OTHER INFORMATION: This sequence represents a viral vector having
      an insert comprising a human immunodeficiency virus sequence, a
      green fluorescent protein variant sequence, a human ubiquitin
      promoter sequence and a woodchuck hepatitis regulator element
      sequence.

<400> SEQUENCE: 9

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat acgcgttgac      240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc    1080
```

```
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctgggaatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aagggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta agggtgcagc ggcctccgcg ccgggttttg gcgcctcccg   2640
cgggcgcccc cctcctcacg cgagcgctg ccacgtcaga cgaagggcgc aggagcgttc   2700
ctgatccttc cgcccggacg ctcaggacag cggcccgctg ctcataagac tcggccttag   2760
aaccccagta tcagcagaag gacattttag gacgggactt gggtgactct agggcactgg   2820
ttttctttcc agagagcgga acaggcgagg aaaagtagtc ccttctcggc gattctgcgg   2880
agggatctcc gtggggcggt gaacgccgat gattatataa ggacgcgccg ggtgtggcac   2940
agctagttcc gtcgcagccg ggatttgggt cgcggttctt gtttgtggat cgctgtgatc   3000
gtcacttggt gagttgcggg ctgctgggct ggccggggct ttcgtggccg ccgggccgct   3060
cggtgggacg gaagcgtgtg gagagaccgc caagggctgt agtctgggtc cgcgagcaag   3120
gttgccctga actgggggtt gggggagcg cacaaaatgg cggctgttcc cgagtcttga   3180
atggaagacg cttgtaaggc gggctgtgag gtcgttgaaa caaggtgggg gcatggtgg   3240
gcggcaagaa cccaaggtct tgaggccttc gctaatgcgg gaaagctctt attcgggtga   3300
gatgggctgg gcaccatct ggggaccctg acgtgaagtt tgtcactgac tggagaactc   3360
gggtttgtcg tctggttgcg ggggcggcag ttatgcggtg ccgttgggca gtgcacccgt   3420
accttttggga gcgcgcgcct cgtcgtgtcg tgacgtcacc cgttctgttg gcttataatg   3480
```

```
cagggtgggg ccacctgccg gtaggtgtgc ggtaggcttt tctccgtcgc aggacgcagg    3540
gttcgggcct agggtaggct ctcctgaatc gacaggcgcc ggacctctgg tgaggggagg    3600
gataagtgag gcgtcagttt ctttggtcgg ttttatgtac ctatcttctt aagtagctga    3660
agctccggtt ttgaactatg cgctcggggt tggcgagtgt gttttgtgaa gttttttagg    3720
caccttttga aatgtaatca tttgggtcaa tatgtaattt tcagtgttag actagtaaag    3780
cttctgcagg tcgactctag aaaattgtcc gctaaattct ggccgttttt ggcttttttg    3840
ttagacagga tccccgggta ccggtcgcca ccatggtgag caagggcgag gagctgttca    3900
ccggggtggt gcccatcctg gtcgagctgg acggcgacgt aaacggccac aagttcagcg    3960
tgtccggcga gggcgagggc gatgccacct acggcaagct gaccctgaag ttcatctgca    4020
ccaccggcaa gctgcccgtg ccctggccca ccctcgtgac caccctgacc tacggcgtgc    4080
agtgcttcag ccgctacccc gaccacatga agcagcacga cttcttcaag tccgccatgc    4140
ccgaaggcta cgtccaggag cgcaccatct tcttcaagga cgacggcaac tacaagaccc    4200
gcgccgaggt gaagttcgag ggcgacaccc tggtgaaccg catcgagctg aagggcatcg    4260
acttcaagga ggacggcaac atcctggggc acaagctgga gtacaactac aacagccaca    4320
acgtctatat catggccgac aagcagaaga acggcatcaa ggtgaacttc aagatccgcc    4380
acaacatcga ggacggcagc gtgcagctcg ccgaccacta ccagcagaac ccccccatcg    4440
gcgacggccc cgtgctgctg cccgacaacc actacctgag cacccagtcc gccctgagca    4500
aagaccccaa cgagaagcgc gatcacatgg tcctgctgga gttcgtgacc gccgccggga    4560
tcactctcgg catggacgag ctgtacaagt aaagcggccg cgactctaga attcgatatc    4620
aagcttatcg ataatcaacc tctggattac aaaatttgtg aaagattgac tggtattctt    4680
aactatgttg ctccttttac gctatgtgga tacgctgctt taatgccttt gtatcatgct    4740
attgcttccc gtatggcttt cattttctcc tccttgtata atcctggtt gctgtctctt    4800
tatgaggagt tgtggcccgt tgtcaggcaa cgtggcgtgg tgtgcactgt gtttgctgac    4860
gcaaccccca ctggttgggg cattgccacc acctgtcagc tcctttccgg gactttcgct    4920
ttccccctcc ctattgccac ggcggaactc atcgccgcct gccttgcccg ctgctggaca    4980
ggggctcggc tgttgggcac tgacaattcc gtggtgttgt cggggaaatc atcgtccttt    5040
ccttggctgc tcgcctgtgt tgccacctgg attctgcgcg gacgtccttc tgctacgtc    5100
ccttcggccc tcaatccagc ggaccttcct tcccgcggcc tgctgccggc tctgcggcct    5160
cttccgcgtc ttcgccttcg ccctcagacg agtcggatct ccctttgggc cgcctccccg    5220
catcgatacc gtcgacctcg agacctagaa aaacatggag caatcacaag tagcaataca    5280
gcagctacca atgctgattg tgcctggcta gaagcacaag aggaggagga ggtgggtttt    5340
ccagtcacac ctcaggtacc tttaagacca atgacttaca aggcagctgt agatcttagc    5400
cacttttta aagaaaaggg gggactgaa gggctaattc actcccaacg aagacaagat    5460
atccttgatc tgtggatcta ccacacacaa ggctacttcc ctgattggca gaactacaca    5520
ccagggccag ggatcagata tccactgacc tttggatggt gctacaagct agtaccagtt    5580
gagcaagaga aggtagaaga agccaatgaa ggagagaaca cccgcttgtt acaccctgtg    5640
agcctgcatg ggatggatga cccggagaga gaagtattag agtggaggtt tgacagccgc    5700
ctagcatttc atcacatggc ccgagagctg catccggact gtactgggtc tctctggtta    5760
gaccagatct gagcctggga gctctctggc taactaggga acccactgct taagcctcaa    5820
```

```
taaagcttgc cttgagtgct tcaagtagtg tgtgcccgtc tgttgtgtga ctctggtaac   5880
tagagatccc tcagacccct ttagtcagtg tggaaaatct ctagcagggc ccgtttaaac   5940
ccgctgatca gcctcgactg tgccttctag ttgccagcca tctgttgttt gcccctcccc   6000
cgtgccttcc ttgacccctgg aaggtgccac tcccactgtc ctttcctaat aaaatgagga   6060
aattgcatcg cattgtctga gtaggtgtca ttctattctg ggggtgggg tggggcagga    6120
cagcaagggg gaggattggg aagacaatag caggcatgct ggggatgcgg tgggctctat   6180
ggcttctgag gcggaaagaa ccagctgggg ctctagggg tatccccacg cgccctgtag    6240
cggcgcatta agcgcggcgg gtgtggtggt tacgcgcagc gtgaccgcta cacttgccag   6300
cgccctagcg cccgctcctt tcgctttctt cccttccttt ctcgccacgt tcgccggctt   6360
tccccgtcaa gctctaaatc ggggctccc tttagggttc cgatttagtg ctttacggca    6420
cctcgacccc aaaaaacttg attagggtga tggttcacgt agtgggccat cgccctgata   6480
gacggttttt cgccctttga cgttggagtc cacgttcttt aatagtggac tcttgttcca   6540
aactggaaca acactcaacc ctatctcggt ctattctttt gatttataag ggattttgcc   6600
gatttcggcc tattggttaa aaaatgagct gatttaacaa aaatttaacg cgaattaatt   6660
ctgtggaatg tgtgtcagtt agggtgtgga aagtccccag gctccccagc aggcagaagt   6720
atgcaaagca tgcatctcaa ttagtcagca accaggtgtg gaaagtcccc aggctcccca   6780
gcaggcagaa gtatgcaaag catgcatctc aattagtcag caaccatagt cccgccccta   6840
actccgccca tcccgcccct aactccgccc agttccgccc attctccgcc ccatggctga   6900
ctaattttt ttatttatgc agaggccgag gccgcctctg cctctgagct attccagaag    6960
tagtgaggag gcttttttgg aggcctaggc ttttgcaaaa agctcccggg agcttgtata   7020
tccattttcg gatctgatca gcacgtgttg acaattaatc atcggcatag tatatcggca   7080
tagtataata cgacaaggtg aggaactaaa ccatggccaa gttgaccagt gccgttccgg   7140
tgctcaccgc gcgcgacgtc gccggagcgg tcgagttctg gaccgaccgg ctcgggttct   7200
cccgggactt cgtggaggac gacttcgccg gtgtggtccg ggacgacgtg accctgttca   7260
tcagcgcggt ccaggaccag gtggtgccgg acaacaccct ggcctgggtg tgggtgcgcg   7320
gcctggacga gctgtacgcc gagtggtcgg aggtcgtgtc cacgaacttc cgggacgcct   7380
ccgggccggc catgaccgag atcggcgagc agccgtgggg gcgggagttc gccctgcgcg   7440
acccggccgg caactgcgtg cacttcgtgg ccgaggagca ggactgacac gtgctacgag   7500
atttcgattc caccgccgcc ttctatgaaa ggttgggctt cggaatcgtt ttccgggacg   7560
ccggctggat gatcctccag cgcggggatc tcatgctgga gttcttcgcc cacccaact   7620
tgtttattgc agcttataat ggttacaaat aaagcaatag catcacaaat ttcacaaata   7680
aagcattttt ttcactgcat tctagttgtg gtttgtccaa actcatcaat gtatcttatc   7740
atgtctgtat accgtcgacc tctagctaga gcttggcgta atcatggtca tagctgtttc   7800
ctgtgtgaaa ttgttatccg ctcacaattc cacacaacat acgagccgga agcataaagt   7860
gtaaagcctg gggtgcctaa tgagtgagct aactcacatt aattgcgttg cgctcactgc   7920
ccgctttcca gtcgggaaac ctgtcgtgcc agctgcatta tgaatcggc caacgcgcgg    7980
ggagaggcgg tttgcgtatt gggcgctctt ccgcttcctc gctcactgac tcgctgcgct   8040
cggtcgttcg gctgcggcga gcggtatcag ctcactcaaa ggcggtaata cggttatcca   8100
cagaatcagg ggataacgca ggaaagaaca tgtgagcaaa aggccagcaa aaggccagga   8160
accgtaaaaa ggccgcgttg ctggcgtttt tccataggct ccgcccccct gacgagcatc   8220
```

```
acaaaaatcg acgctcaagt cagaggtggc gaaacccgac aggactataa agataccagg    8280
cgtttccccc tggaagctcc ctcgtgcgct ctcctgttcc gaccctgccg cttaccggat    8340
acctgtccgc ctttctccct cgggaagcg tggcgctttc tcatagctca cgctgtaggt    8400
atctcagttc ggtgtaggtc gttcgctcca agctgggctg tgtgcacgaa ccccccgttc    8460
agcccgaccg ctgcgcctta tccggtaact atcgtcttga gtccaacccg gtaagacacg    8520
acttatcgcc actggcagca gccactggta acaggattag cagagcgagg tatgtaggcg    8580
gtgctacaga gttcttgaag tggtggccta actacggcta cactagaaga acagtatttg    8640
gtatctgcgc tctgctgaag ccagttacct tcggaaaaag agttggtagc tcttgatccg    8700
gcaaacaaac caccgctggt agcggtggtt ttttgtttg caagcagcag attacgcgca     8760
gaaaaaaagg atctcaagaa gatcctttga tcttttctac ggggtctgac gctcagtgga    8820
acgaaaactc acgttaaggg attttggtca tgagattatc aaaaaggatc ttcacctaga    8880
tccttttaaa ttaaaaatga agttttaaat caatctaaag tatatatgag taaacttggt    8940
ctgacagtta ccaatgctta atcagtgagg cacctatctc agcgatctgt ctatttcgtt    9000
catccatagt tgcctgactc cccgtcgtgt agataactac gatacgggag ggcttaccat    9060
ctggccccag tgctgcaatg ataccgcgag acccacgctc accggctcca gatttatcag    9120
caataaacca gccagccgga agggccgagc gcagaagtgg tcctgcaact ttatccgcct    9180
ccatccagtc tattaattgt tgccgggaag ctagagtaag tagttcgcca gttaatagtt    9240
tgcgcaacgt tgttgccatt gctacaggca tcgtggtgtc acgctcgtcg tttggtatgg    9300
cttcattcag ctccggttcc caacgatcaa ggcgagttac atgatccccc atgttgtgca    9360
aaaaagcggt tagctccttc ggtcctccga tcgttgtcag aagtaagttg gccgcagtgt    9420
tatcactcat ggttatggca gcactgcata attctcttac tgtcatgcca tccgtaagat    9480
gcttttctgt gactggtgag tactcaacca agtcattctg agaatagtgt atgcggcgac    9540
cgagttgctc ttgcccggcg tcaatacggg ataataccgc gccacatagc agaactttaa    9600
aagtgctcat cattggaaaa cgttcttcgg ggcgaaaact ctcaaggatc ttaccgctgt    9660
tgagatccag ttcgatgtaa cccactcgtg cacccaactg atcttcagca tctttactt    9720
tcaccagcgt ttctgggtga gcaaaaacag gaaggcaaaa tgccgcaaaa aagggaataa    9780
gggcgacacg gaaatgttga atactcatac tcttcctttt tcaatattat tgaagcattt    9840
atcagggtta ttgtctcatg agcggataca tatttgaatg tatttagaaa aataaacaaa    9900
taggggttcc gcgcacattt ccccgaaaag tgccacctga c                        9941
```

METHOD FOR PRODUCING TRANSGENIC RATS

REFERENCE TO RELATED APPLICATIONS

The present application claims priority under 35 U.S.C. §120 as a continuation of U.S. application Ser. No. 10/243,820 filed Sep. 13, 2002 which in turn claims priority under 35 U.S.C. §119(e) to U.S. Provisional Application No. 60/322,031, filed Sep. 13, 2001 and to U.S. Provisional Application No. 60/347,782, filed Jan. 9, 2002.

STATEMENT OF GOVERNMENT SUPPORT

This invention was made with government support under Grant Number GM39458 awarded by the National Institutes of Health. The United States Government has certain rights in the invention.

All of the priority applications are hereby incorporated by reference in their entirety.

BACKGROUND OF THE INVENTION

1. Field of the Invention

The present invention relates to methods for generating transgenic animals, particularly transgenic birds and fish, using viral constructs engineered to carry the transgene(s) of interest.

2. Description of the Related Art

Early transgenic experiments used an oncoretrovirus to introduce the gene of interest into embryonic cells (Jaenisch Proc. Natl. Acad. Sci. USA 73:1260-1264 (1976)). In a typical experiment an engineered Moloney strain of mouse leukemia virus (MoMLV) was injected into the blastocyst cavity of mice. While the transgene was often integrated into the genome of the resulting mice, no gene expression could be detected.

Today, the majority of transgenic animals are made using direct injection technology (Gordon and Ruddle Science 214:1244-1246 (1981)). Briefly, a DNA construct carrying the gene of interest is injected directly into the pronucleus of a single-cell zygote. The cell is then implanted into a pseudopregnant female and the resulting progeny is analyzed for expression of the gene.

While this method achieves both integration and expression of the transgene, there are a number of significant drawbacks to the direct injection technique. First, in order to carry out the technique it is necessary to inject DNA directly into the pronucleus. This is possible in some specific strains of mice, such as Black6×BDA, because the male pronucleus is visible. However, in other animals and other strains of mice the pronucleus is less visible, making the technique extremely difficult. Further, the injection requires the assistance of a skilled technician and a significant investment in equipment; micromanipulators are necessary to hold the cell and the injection pipette and a pressure source is required that can deliver picoliter amounts of DNA solution.

A second equally significant problem with the direct injection method is the low percentage of injected zygotes that produce transgenic animals. The injection pipette must go through the zona pellucida, the cell membrane and the nuclear envelope. Thus only 80-90% of mouse cells survive the injection. Other animal cells are less hardy and the survival rates are somewhat lower, with about 60% survival for rats and 40-50% for cows. In mice, of the original zygotes, about 25% are successfully injected and implanted in a pseudopregnant female. About 20% of the resulting animals have the transgene integrated into their genome. Of these, about 20% will express the gene. However, even if the animals express the gene, it is possible that the expression pattern will not be useful. Thus, only about 1% of injected zygotes result in transgenic animals that express the gene of interest. This low efficiency of transgenesis is particularly troubling for larger animals, such as pigs, cows or goats, in which obtaining large numbers of embryos is not possible (see, e.g., Wall et al. J. Cell. Biochem. 49:113 (1992)).

In addition, direct pronuclear injection is not possible for many types of animals, including birds.

SUMMARY OF THE INVENTION

One aspect of the present invention concerns a method of producing a transgenic animal, preferably a transgenic bird or a transgenic fish. In one embodiment a method is provided for producing a transgenic bird, the method comprising transfecting a packaging cell line with a retroviral construct, recovering recombinant retrovirus, and infecting a fertilized bird egg with the recombinant retrovirus.

In one embodiment infecting a bird egg comprises contacting the embryonic blastodisc of the bird egg with the retroviral particles.

The retroviral construct preferably comprises the R and U5 sequences from a 5' lentiviral long terminal repeat (LTR) and a self-inactivating lentiviral 3' LTR. Further, the self-inactivating 3' LTR preferably comprises a U3 element with a deletion of its enhancer sequence. In one embodiment the LTR sequences are from HIV.

In one embodiment the retroviral construct comprises a gene that is desirably expressed in the transgenic bird. In this embodiment the retroviral construct may also comprise an internal promoter and/or enhancer. In one embodiment the internal promoter is ubiquitous. The ubiquitous promoter may be any ubiquitous promoter known in the art. For example, the ubiquitous promoter may be selected from the group consisting of the ubiquitin promoter, the CMV β-actin promoter and the pgk promoter. In another embodiment the internal promoter is tissue-specific. The tissue specific promoter may be any tissue specific promoter known in the art, for example, a promoter selected from the group consisting of the lck promoter, the myogenin promoter and the thy1 promoter.

In addition, the recombinant retrovirus may be pseudotyped. Thus, in one embodiment the recombinant retrovirus is pseudotyped with the vesicular stomatitis virus envelope glycoprotein.

The viral construct may comprise one or more additional genetic elements. In one embodiment the viral construct comprises a promoter operably linked to the R and U5 5' LTR sequences, preferably a CMV promoter sequence. An enhancer, preferably a CMV enhancer sequence, may also be included in the viral construct.

In another embodiment the viral construct comprises a woodchuck hepatitis virus enhancer element sequence. In yet another embodiment the viral construct comprises a tRNA amber suppressor sequence.

The viral construct may additionally comprise a reporter gene operably linked to the internal promoter. The reporter gene may encode be a fluorescent protein, preferably green fluorescent protein.

In another aspect the invention concerns a method of producing a transgenic bird comprising opening a window in the shell of a fertilized bird egg, injecting modified retrovirus into the space between the perivitelline membrane and the embryonic blastodisc and incubating the embryo until hatching. The modified retrovirus is preferably a modified lentivirus. The modified lentivirus is preferably produced by transfecting a packaging cell line with a viral construct. In one embodiment the viral construct comprises the R and U5 sequences from a lentiviral 5' LTR, an internal promoter, a gene of interest and a self inactivating lentiviral 3' LTR.

In yet another aspect the invention concerns a transgenic bird made by any of the disclosed methods. Thus, the transgenic bird preferably comprises one or more cells, preferably germ cells, that comprise proviral DNA. The proviral DNA may comprise a self-inactivating lentiviral 3' LTR, such as a self-inactivating HIV 3' LTR. In particular, the self-inactivating 3' LTR may have a deletion of its enhancer sequence.

In another embodiment a transgenic fish is produced by a method that comprises transfecting a packaging cell line with a viral construct, recovering recombinant retroviral particles, and infecting a fish egg with the recombinant retroviral particles. Preferably the viral construct comprises the R and U5 sequences from a 5' lentiviral LTR and a self-inactivating 3' lentiviral LTR. Infecting the fish egg preferably comprises delivering the retroviral particles to the space between the chorion and the cell membrane of the fish egg.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 4 shows ubiquitous GFP expression in rats derived from the delivery of modified lentivirus to single-cell embryos in vitro.

Figure 12:
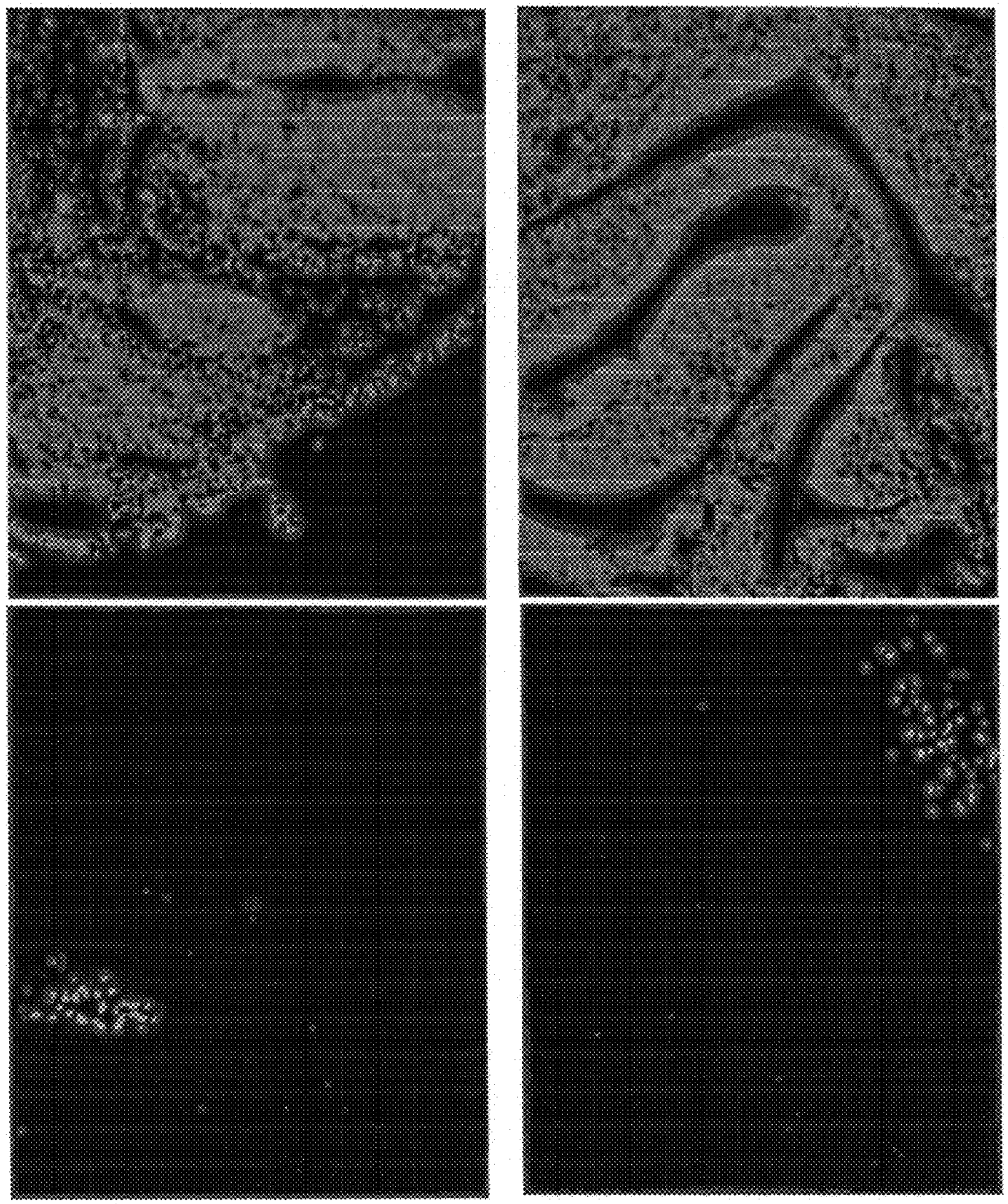

FIG. 12 also shows immunofluorescence with an antibody against GFP in cross sections of an E11.5 embryo carrying a myogenin promoter driving H2B-GFP. Lack of staining in the viscera is noteworthy.

Figure 13:
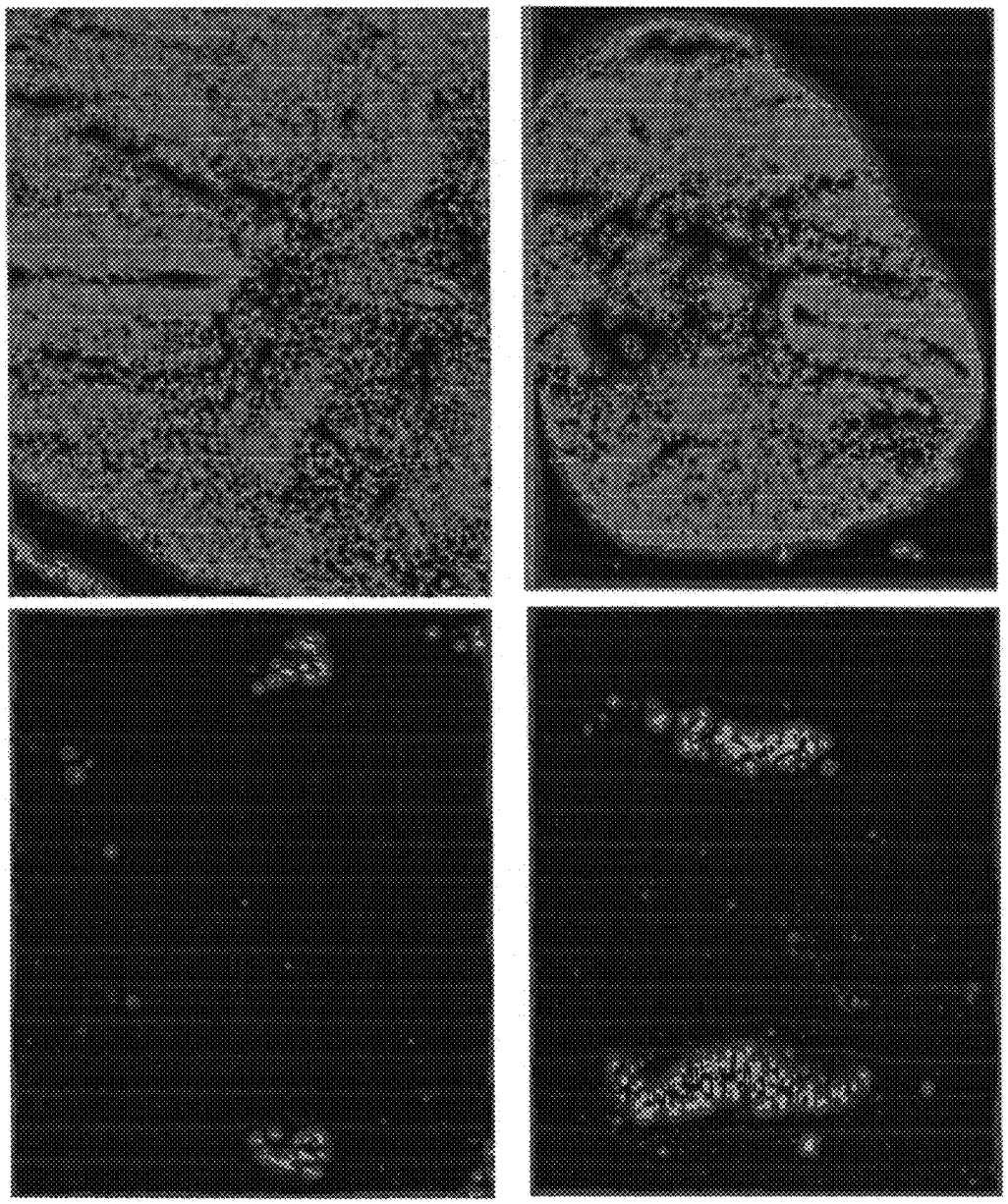

FIG. 13 also shows immunofluorescence with an antibody against GFP in cross sections of an E11.5 embryo carrying a myogenin promoter driving H2B-GFP. Specific staining of somites on either side of the neural tube can be visualized.

Figure 14:
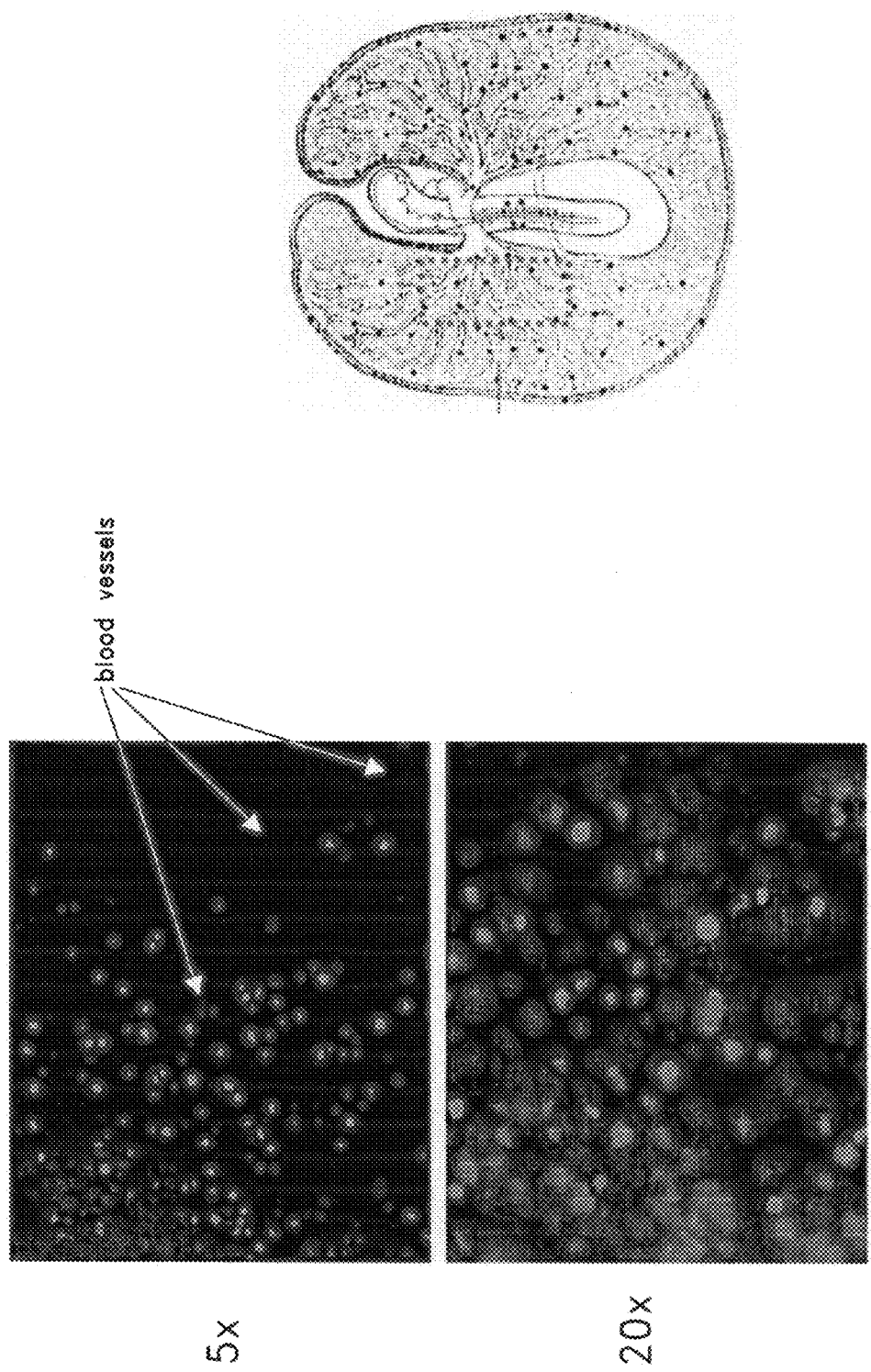

FIG. 14 shows H2B-GFP expression in the extraembryonic tissue of developing zebra finch.

Figure 15:
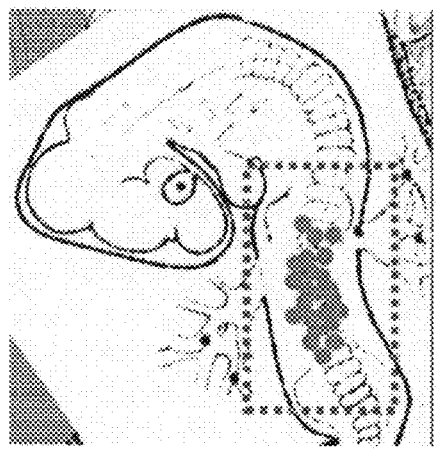
Figure 15:
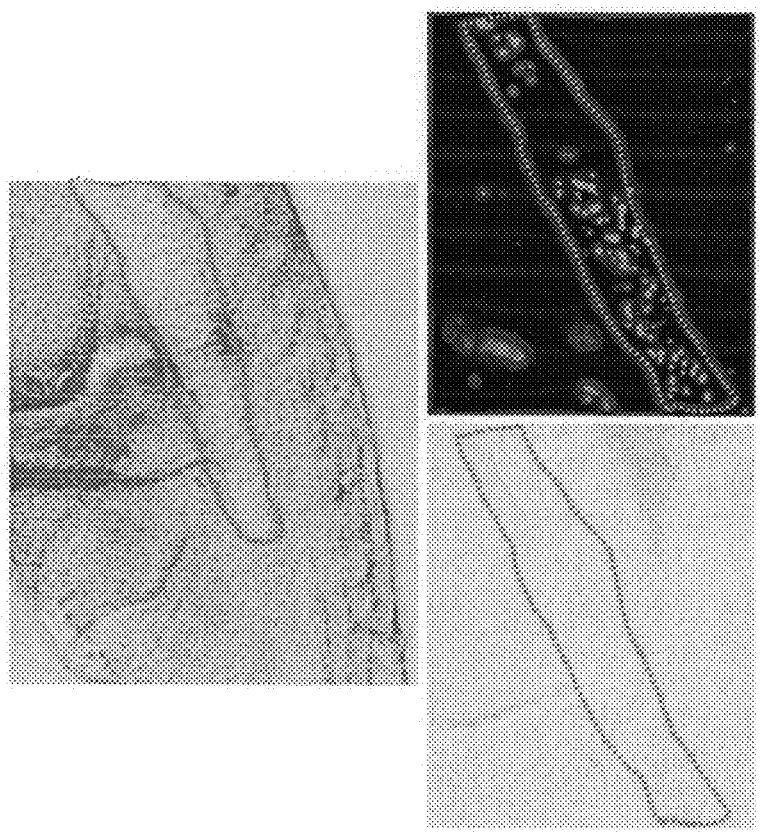

FIG. 15 shows H2B-GFP expression inside of the zebra finch embryo.

FIG. 16 shows the nucleotide sequence of GFP.

FIG. 17 shows the nucleotide sequence of H2B-GFP.

FIG. 18A shows the nucleotide sequence of HIV NL4.3 flap and 18B shows the nucleotide sequence of WRE.

FIG. 19A shows the nucleotide sequence of the myogenin promoter and 19B shows a partial nucleotide sequence of the Lck promoter.

FIG. 20 shows the nucleotide sequence of the human ubiquitin promoter.

FIG. 21 shows the nucleotide sequence of the HIV-1 flap+ ubiquitin+GFP+WRE construct.

DETAILED DESCRIPTION OF THE PREFERRED EMBODIMENT

Retroviruses are enveloped RNA viruses that are capable of infecting animal cells. When a retrovirus infects a cell, its RNA genome is converted into a double-stranded linear DNA form by reverse transcription. The DNA form is integrated into the host cell genome as a provirus. The present invention is based on the discovery that recombinant retroviruses can be used to create transgenic animals. Transgenic animals resulting from the methods of the present invention have one or more copies of the transgene of interest integrated in their genome.

Previous transgenic technology is not commercially practical in larger animals, such as monkeys, dogs, poultry, cows, pigs or sheep. Furthermore, previous transgenic methods are not applicable to poultry. Thus, the methods of the present invention will find great commercial application, for example in biotechnology and agriculture. The present methods may be used to introduce the gene of choice into animals in order to confer upon them desired attributes. For example, the described methods may be used to confer disease resistance. In biotechnology, the ability to rapidly develop large numbers of transgenic animals, particular higher order animals such as monkeys, will allow for the analysis of gene function and the evaluation of compounds that potentially modulate gene expression, protein function, or are useful in treating a disease or disorder. Two types of assays in which the methods of the present invention are particularly useful are gene trap assays and large-scale mutagenesis screens, each of which is described below.

Unless defined otherwise, all technical and scientific terms used herein have the same meaning as commonly understood by one of ordinary skill in the art to which this invention belongs. Any methods, devices and materials similar or equivalent to those described herein can be used in the practice of this invention.

By "transgene" is meant any nucleotide or DNA sequence that is integrated into one or more chromosomes of a host cell by human intervention, such as by the methods of the present invention. In one embodiment the transgene comprises a "gene of interest." A "gene of interest" is a nucleic acid sequence that encodes a protein or other molecule that is desirable for integration and/or expression in a host cell. In this embodiment the gene of interest is generally operatively linked to other sequences that are useful for obtaining the desired expression of the gene of interest, such as transcriptional regulatory sequences. In another embodiment the transgene can be a DNA sequence that is used to mark the chromosome where it has integrated. In this situation, the transgene does not have to comprise a gene that encodes a protein that can be expressed. This use of the transgene as a molecular tag has numerous applications, for example for mutagenesis studies as described below.

The term "transgenic" is used herein to describe the property of harboring a transgene. For instance, a "transgenic organism" is any animal, including mammals, fish, birds and amphibians, in which one or more of the cells of the animal contain nucleic acid introduced by way of human intervention, such as by the methods described herein. In the typical transgenic animal, the transgene causes the cell to express or overexpress a recombinant protein. However for some applications, such as the mutagenesis studies described below, it is not necessary or desirable for the transgenic organism to express a recombinant protein.

The terms "founder," "founder animal" and "founder line" refer to those animals that are mature products of the embryos or oocytes to which the transgene was added, i.e. those animals that grew from the embryos or oocytes into which DNA was inserted.

The terms "progeny" and "progeny of the transgenic animal" refer to any and all offspring of every generation subsequent to the originally transformed animal.

The term "animal" is used in its broadest sense and refers to all animals including mammals, birds, fish, reptiles and amphibians.

The term "mammal" refers to all members of the class Mammalia and includes any animal classified as a mammal, including humans, domestic and farm animals, and zoo, sports or pet animals, such as mouse, rabbit, pig, sheep, goat, cattle and higher primates.

The term "oocyte" refers to a female gamete cell and includes primary oocytes, secondary oocytes and mature, unfertilized ovum. As used herein, the term "egg" when used in reference to a mammalian egg, means an oocyte surrounded by a zona pellucida. The term "zygote" refers to a fertilized ovum. The term "embryo" broadly refers to an animal in the early stages of development.

"Perivitelline space" refers to the space located between the zona pellucida and the cell membrane of a mammalian egg or embryonic cell.

"Target cell" or "host cell" means a cell that is to be transformed using the methods and compositions of the invention.

"Lentivirus" refers to a genus of retroviruses that are capable of infecting dividing and non-dividing cells. Several examples of lentiviruses include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates.

A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. See, for example, "RNA Viruses: A Practical Approach" (Alan J. Cann, Ed., Oxford University Press, (2000)), O Narayan and Clements J. Gen. Virology 70:1617-1639 (1989), Fields et al. Fundamental Virology Raven Press. (1990), Miyoshi H, Blomer U, Takahashi M, Gage F H, Verma I M. *J. Virol.* 72(10):8150-7 (1998), U.S. Pat. No. 6,013,516.

"Virion," "viral particle" and "retroviral particle" are used herein to refer to a single virus comprising an RNA genome, pol gene derived proteins, gag gene derived proteins and a lipid bilayer displaying an envelope (glyco)protein. The RNA genome is usually a recombinant RNA genome and thus may contain an RNA sequence that is exogenous to the native viral genome. The RNA genome may also comprise a defective endogenous viral sequence.

A "pseudotyped" retrovirus is a retroviral particle having an envelope protein that is from a virus other than the virus from which the RNA genome is derived. The envelope protein may be from a different retrovirus or from a non-retroviral virus. A preferred envelope protein is the vesicular stomatitius virus G (VSV G) protein. However, to eliminate the possibility of human infection, viruses can alternatively be pseudotyped with ecotropic envelope protein that limit infection to a specific species, such as mice or birds.

The term "provirus" is used to refer to a duplex DNA sequence present in a eukaryotic chromosome that corresponds to the genome of an RNA retrovirus. The provirus may be transmitted from one cell generation to the next without causing lysis or destruction of the host cell.

A "self-inactivating 3' LTR" is a 3' long terminal repeat (LTR) that contains a mutation, substitution or deletion that prevents the LTR sequences from driving expression of a downstream gene. A copy of the U3 region from the 3' LTR acts as a template for the generation of both LTR's in the integrated provirus. Thus, when the 3' LTR with an inactivating deletion or mutation integrates as the 5' LTR of the provirus, no transcription from the 5' LTR is possible. This eliminates competition between the viral enhancer/promoter and any internal enhancer/promoter. Self-inactivating 3' LTRs are described, for example, in Zufferey et al. *J. Virol.* 72:9873-9880 (1998), Miyoshi et al. *J. Virol.* 72:8150-8157 and Iwakuma et al. *Virology* 261:120-132 (1999).

In one aspect of the invention, a recombinant retrovirus is used to deliver a transgene of interest to a cell, preferably an oocyte or an embryonic cell, more preferably a one-cell embryo. The transgene, and any associated genetic elements, are thus integrated into the genome of the host cell as a provirus. The cell may then be allowed to develop into a transgenic animal.

The recombinant retrovirus used to deliver the transgene is preferably a modified lentivirus, and thus is able to infect both dividing and non-dividing cells. The recombinant retrovirus preferably comprises a modified lentiviral genome that includes the transgene. Further, the modified lentiviral genome preferably lacks endogenous genes for proteins required for viral replication, thus preventing replication in the transgenic animal. The required proteins are provided in trans in the packaging cell line during production of the recombinant retrovirus, as described below.

In the preferred embodiment the transgene is incorporated into a viral construct that comprises an intact retroviral 5' LTR and a self-inactivating 3' LTR. The viral construct is preferably introduced into a packaging cell line that packages viral genomic RNA based on the viral construct into viral particles with the desired host specificity. Viral particles are collected and allowed to infect the host cell. Each of these aspects is described in detail below.

The Viral Construct

The viral construct is a nucleotide sequence that comprises sequences necessary for the production of recombinant retrovirus in a packaging cell. In one embodiment the viral construct additionally comprises genetic elements that allow for the desired expression of a gene of interest in the host.

Generation of the viral construct can be accomplished using any suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)).

The viral construct may incorporate sequences from the genome of any known organism. The sequences may be incorporated in their native form or may be modified in any way. For example, the sequences may comprise insertions, deletions or substitutions. In the preferred embodiment the viral construct comprises sequences from a lentivirus genome, such as the HIV genome or the SIV genome.

The viral construct preferably comprises sequences from the 5' and 3' LTRs of a lentivirus. More preferably the viral construct comprises the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Preferably the LTR sequences are HIV LTR sequences.

The viral construct preferably comprises an inactivated or self-inactivating 3' LTR. The 3' LTR may be made self-inactivating by any method known in the art. In the preferred embodiment the U3 element of the 3' LTR contains a deletion of its enhancer sequence, preferably the TATA box, Sp1 and NF-kappa B sites. As a result of the self-inactivating 3' LTR, the provirus that is integrated into the host cell genome will comprise an inactivated 5' LTR.

Optionally, the U3 sequence from the lentiviral 5' LTR may be replaced with a promoter sequence in the viral construct. This may increase the titer of virus recovered from the packaging cell line. An enhancer sequence may also be included. Any enhancer/promoter combination that increases expression of the viral RNA genome in the packaging cell line may be used. In the preferred embodiment the CMV enhancer/promoter sequence is used.

In one embodiment the viral construct comprises a gene that encodes a protein that is desirably expressed in one or more cells of a transgenic animal. Preferably the gene of interest is located between the 5' LTR and 3' LTR sequences. Further, the gene of interest is preferably in a functional relationship with other genetic elements, for example transcription regulatory sequences such as promoters and/or enhancers, to regulate expression of the gene of interest in a particular manner once the transgene is incorporated into the host genome. In certain embodiments, the useful transcriptional regulatory sequences are those that are highly regulated with respect to activity, both temporally and spatially.

Preferably the gene of interest is in a functional relationship with internal promoter/enhancer regulatory sequences. An "internal" promoter/enhancer is one that is located between the 5' LTR and the 3' LTR sequences in the viral construct and is operably linked to the gene that is desirably expressed.

The internal promoter/enhancer may be any promoter, enhancer or promoter/enhancer combination known to increase expression of a gene with which it is in a functional relationship. A "functional relationship" and "operably linked" mean, without limitation, that the gene is in the correct location and orientation with respect to the promoter and/or enhancer that expression of the gene will be affected when the promoter and/or enhancer is contacted with the appropriate molecules.

The internal promoter/enhancer is preferably selected based on the desired expression pattern of the gene of interest and the specific properties of known promoters/enhancers. Thus, the internal promoter may be a constitutive promoter. Non-limiting examples of constitutive promoters that may be used include the promoter for ubiquitin, CMV (Karasuyama et al J. Exp. Med. 169:13 (1989), β-actin (Gunning et al. Proc. Natl. Acad. Sci. USA 84:4831-4835 (1987) and pgk (see, for example, Adra et al. Gene 60:65-74 (1987), Singer-Sam et al. Gene 32:409-417 (1984) and Dobson et al. Nucleic Acids Res. 10:2635-2637 (1982)). Alternatively, the promoter may be a tissue specific promoter. Several non-limiting examples of tissue specific promoters that may be used include lck (see, for example, Garvin et al. Mol. Cell. Biol. 8:3058-3064 (1988) and Takadera et al. Mol. Cell. Biol. 9:2173-2180 (1989)), myogenin (Yee et al. Genes and Development 7:1277-1289 (1993), and thy1 (Gundersen et al. Gene 113: 207-214 (1992). In addition, promoters may be selected to allow for inducible expression of the transgene. A number of systems for inducible expression using such a promoter are known in the art, including the tetracycline responsive system and the lac operator-repressor system. It is also contemplated that a combination of promoters may be used to obtain the desired expression of the gene of interest. The skilled artisan will be able to select a promoter based on the desired expression pattern of the gene in the resulting transgenic animal.

An internal enhancer may also be present in the viral construct to increase expression of the gene of interest. For example the CMV enhancer (Karasuyama et al J. Exp. Med. 169:13 (1989) may be used in combination with the chicken β-actin promoter. Again, one of skill in the art will be able to select the appropriate enhancer based on the desired expression pattern.

The gene of interest is not limited in any way and includes any gene that the skilled practitioner desires to have integrated and/or expressed in a transgenic animal. For example, the gene of interest may be one that encodes a protein that modifies a physical characteristic of the transgenic animal, such as a protein that modifies size, growth, or tissue composition. In another example the gene of interest may encode a protein of commercial value that may be harvested from the transgenic animal.

In addition, more than one gene of interest may be placed in functional relationship with the internal promoter. For example a gene encoding a marker protein may be placed after the primary gene of interest to allow for identification of cells that are expressing the desired protein. In one embodiment a fluorescent marker protein, preferably green fluorescent protein (GFP), is incorporated into the construct along with the gene of interest. If a second reporter gene is included, an internal ribosomal entry site (IRES) sequence is also preferably included. The IRES sequence may facilitate the expression of the reporter gene The viral construct may also contain additional genetic elements. The types of elements that may be included in the construct are not limited in any way and will be chosen by the skilled practitioner to achieve a particular result. For example, a signal that facilitates nuclear entry of the viral genome in the target cell may be included. An example of such a signal is the HIV-1 flap signal.

Further, elements may be included that facilitate the characterization of the provirus integration site in the genome of the animal. For example, a tRNA amber suppressor sequence may be included in the construct.

In addition, the construct may contain one or more genetic elements designed to enhance expression of the gene of interest. For example, a woodchuck hepatitis virus responsive element (WRE) may be placed into the construct (Zufferey et al. J. Virol. 74:3668-3681 (1999); Deglon et al. Hum. Gene Ther. 11:179-190 (2000)).

A chicken β-globin insulator may also be included in the viral construct. This element has been shown to reduce the chance of silencing the integrated provirus in the transgenic animal due to methylation and heterochromatinization effects. In addition, the insulator may shield the internal enhancer, promoter and exogenous gene from positive or negative positional effects from surrounding DNA at the integration site on the chromosome.

Any additional genetic elements are preferably inserted 3' of the gene of interest.

In a specific embodiment, the viral vector comprises: a cytomegalovirus (CMV) enhancer/promoter sequence; the R and U5 sequences from the HIV 5' LTR; the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR.

The viral construct is preferably cloned into a plasmid that may be transfected into a packaging cell line. The preferred plasmid preferably comprises sequences useful for replication of the plasmid in bacteria.

Production of Virus

Any method known in the art may be used to produce infectious retroviral particles whose genome comprises an RNA copy of the viral construct described above.

Preferably, the viral construct is introduced into a packaging cell line. The packaging cell line provides the viral proteins that are required in trans for the packaging of the viral genomic RNA into viral particles. The packaging cell line may be any cell line that is capable of expressing retroviral proteins. Preferred packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430). The most preferable cell line is the 293 cell line.

The packaging cell line may stably express the necessary viral proteins. Such a packaging cell line is described, for example, in U.S. Pat. No. 6,218,181. Alternatively a packaging cell line may be transiently transfected with plasmids comprising nucleic acid that encodes the necessary viral proteins.

In one embodiment a packaging cell line that stably expresses the viral proteins required for packaging the RNA genome is transfected with a plasmid comprising the viral construct described above.

In another embodiment a packaging cell line that does not stably express the necessary viral proteins is co-transfected with two or more plasmids essentially as described in Yee et al. (*Methods Cell. Biol.* 43A, 99-112 (1994)). One of the plasmids comprises the viral construct comprising the transgene. The other plasmid(s) comprises nucleic acid encoding the proteins necessary to allow the cells to produce functional virus that is able to infect the desired host cell.

The packaging cell line may not express envelope gene products. In this case the packaging cell line will package the viral genome into particles that lack an envelope protein. As the envelope protein is responsible, in part, for the host range of the viral particles, the viruses are preferably pseudotyped. Thus the packaging cell line is preferably transfected with a plasmid comprising sequences encoding a membrane-associated protein that will permit entry of the virus into a host cell. One of skill in the art will be able to choose the appropriate pseudotype for the host cell that is to be used. For example, in one embodiment the viruses are pseudotyped with the vesicular stomatitis virus envelope glycoprotein (VSVg). In another embodiment, a mutant ecotropic envelope protein is used, such as the ecotropic envelope protein 4.17 (Powell et al. Nature Biotechnology 18(12):1279-1282 (2000)). In addition to conferring a specific host range the pseudotype may permit the virus to be concentrated to a very high titer and may enhance safety by preventing the virus from infecting undesired cell types.

In the preferred embodiment a packaging cell line that does not stably express viral proteins is transfected with the viral construct, a second vector comprising the HIV-1 packaging vector with the env, nef 5'LTR, 3'LTR and vpu sequences deleted, and a third vector encoding an envelope glycoprotein. Preferably the third vector encodes the VSVg envelope glycoprotein.

The recombinant virus is then preferably purified from the packaging cells, titered and diluted to the desired concentration.

Transgenic Animals

In order to make transgenic animals, an oocyte or one or more embryonic cells are infected with the recombinant virus produced as described above. One of skill in the art will recognize that the method of infection and the treatment of the cell following infection will depend upon the type of animal from which the cell is obtained. For example, mammalian cells are preferably implanted in a pseudopregnant female following infection while for the generation of transgenic birds or fish, the virus is preferably delivered to a laid egg and thus implantation is not required.

While early methods of making transgenic animals required the cells to be rapidly dividing, there is no such requirement in the methods of the present invention. Thus the cell may be contacted at any point in development. In the preferred embodiment, a zygote is contacted with the recombinant virus.

The cells to be infected with the virus may be obtained by any method known in the art and appropriate for the specific species in which it is desired to make a transgenic animal. For example, the recovery of fertilized mouse oocytes is described in Hogan et al. (Manipulating the Mouse Embryo: A Laboratory Manual. $2^{nd}$ ed. Cold Spring Harbor Laboratory Press, NY (1994)). A method for obtaining fertilized rat oocytes is described in Armstrong et al. (Biol. Reprod. 39, 511-518 (1998)).

It is not necessary that the cells be contacted after fertilization. In one embodiment, the virus is delivered to unfertilized ova. Development may then be initialized, for example by in vitro fertilization.

Delivery of the Virus

The virus may be delivered to the cell in any way that allows the virus to infect the cell. Preferably the virus is allowed to contact the cell membrane. Two preferred methods of delivering the virus to mammalian cells, injection and direct contact, are described below.

Injection

In a first embodiment the virus is injected into the perivitelline space between the zona pellucida and the cell membrane of a single-cell zygote. Preferably less than 50 picoliters of viral suspension is injected, more preferably less than 25 picoliters and even more preferably about 10 picoliters.

The virus is preferably present in a viral suspension and may be injected by any method known in the art. The viral suspension is preferably injected through a hydraulic injector. More preferably a glass micropipette is used to inject the virus. In one embodiment a micropipette is prepared by pulling borosilicate glass capillary on a pipette puller. The tip is preferably opened and beveled to approximately 10 μm. The lentiviral suspension may be loaded into the micropipette from the tip using gentle negative pressure.

In one embodiment the cell is stabilized with a holding pipette mounted on a micromanipulator, such as by gentle negative pressure against a fire-polished pipette, and a second micromanipulator is used to direct the tip of a micropipette into the space between the zona pellucida and the cell membrane, where the virus is injected.

Direct Contact

In another embodiment the zona pellucida is removed from the cell to produce a denuded embryo and the cell membrane is contacted with the virus. The zona pellucida may be removed by any method known in the art. Preferably it is removed by enzymatic treatment. For example, treatment with pronase may be used to remove the zona pellucida while the cell membrane is kept intact. Alternatively, the cell may be placed in media at pH at which the zona pellucida dissolves while the cell membrane remains intact. For example the cell may be incubated in an acidic Tyrode's solution at room temperature for several minutes. Once the zona pellucida is removed, any method that allows for the virus to contact the cell membrane may be used. Preferably, the cell is incubated in a solution containing the virus. Even more preferably, the solution is media that facilitates survival of the cell.

In this embodiment, the cells are preferably contacted with the virus in culture plates. The virus may be suspended in media and added to the wells of a multi-well culture plate. The cells may then be plated in the individual wells. The media containing the virus may be added prior to the plating of the cells or after the cells have been plated. Preferably individual cells are incubated in approximately 10 μl of media. However, any amount of media may be used as long as an appropriate concentration of virus in the media is maintained such that infection of the host cell occurs.

The cells are preferably incubated with the virus for a sufficient amount of time to allow the virus to infect the cells.

Preferably the cells are incubated with virus for at least 1 hour, more preferably at least 5 hours and even more preferably at least 10 hours.

Both the injection and direct contact embodiments may advantageously be scaled up to allow high throughput transgenesis. Because of the relative simplicity of the injection technique, it is possible to inject many embryos rapidly. For example, it is possible to inject more than 200 fertilized oocytes in less than one hour. With regard to the direct contact embodiment, any number of embryos may be incubated in the viral suspension simultaneously. This may be accomplished, for example, by plating the desired number of single-cell zygotes in multi-well tissue culture plates containing the virus suspended in media appropriate for the survival and growth of the cells.

In both embodiments, any concentration of virus that is sufficient to infect the cell may be used. Preferably the concentration is at least 1 pfu/µl, more preferably at least 10 pfu/µl, even more preferably at least 400 pfu/µl and even more preferably at least $1 \times 10^4$ pfu/µl.

Following infection with the virus, the cells are preferably implanted in an animal. More preferably cells infected with the virus are implanted in pseudo-pregnant animals of the same species from which the infected cells were obtained. Methods of creating pseudo-pregnancy in animals and implanting embryos are well known in the art and are described, for example, in Hogan et al. (Manipulating the Mouse Embryo: A Laboratory Manual. $2^{nd}$ ed. Cold Spring Harbor Laboratory Press, NY (1994)).

In the preferred embodiment early stage embryos (approximately 0-2.5 days p.c.) still with an intact zona pellucida are transferred to the oviduct of timed pseudopregnant female (preferably 0.5 days p.c.), while embryos that have reached the blastocyst stage are transferred to the uterus of timed pseudopregnant females (preferably 2.5 days p.c.). Denuded embryos are preferably cultured in vitro until they reach the morula or blastocyst stage (48 to 72 hours in culture), and are then implanted into appropriately timed pseudopregnant females.

The embryos and resulting animals may be analyzed, for example for integration of the transgene, the number of copies of the transgene that integrated, the location of the integration, the ability to transmit the transgene to progeny and expression of the transgene. Such analysis may be carried out at any time and may be carried out by any methods known in the art. Standard techniques are described, for example, in Hogan et al. (supra).

The methods of infecting cells disclosed above do not depend upon species-specific characteristics of the cells. As a result, they are readily extended to all mammalian species.

Initial experiments with mice indicate that of those animals that develop to full term, 80-90% carried at least one copy of the transgene and that, of these, approximately 85% express the gene of interest. Of the transgenic animals about 25% carry only 1 or 2 copies of the transgene. The highest number of proviral insertions observed was about 30. Of the animals that carried only 1 or 2 copies of the transgene, about 80% expressed the gene of interest.

As discussed above, the modified retrovirus can be pseudotyped to confer upon it a broad host range. One of skill in the art would also be aware of appropriate internal promoters to achieve the desired expression of a gene of interest in a particular animal species. Thus, one of skill in the art will be able to modify the method of infecting cells to create transgenic animals of any species.

For example, transgenic birds are created by delivering a modified retrovirus, as described above, to the primordial germ cells of early stage avian embryos. In one embodiment, freshly laid eggs are obtained and placed in a temperature controlled, humidified incubator. Preferably, the embryonic blastodisc in the egg is gradually rotated to lie on top of the yolk. This may be accomplished by any method known in the art, such as by gently rocking the egg regularly, preferably every 15 minutes. Approximately 36 hours later, the modified retrovirus is delivered into the space between the embryonic disk and the perivitelline membrane. Preferably about 50 nL of viral solution is delivered, more preferably about 100 nL of viral solution is delivered, and even more preferably about 200 nL of viral solution is delivered. The viral solution may be delivered by any method known in the art for delivering compositions to the inside of an egg. In the preferred embodiment a window is opened in the shell, the viral solution is injected through the window and the shell window is closed. The eggs are preferably incubated until hatching. The eggs will hatch after approximately 20 days, depending upon the particular avian species from which they are obtained. Hatched chicks are preferably raised to sexual maturity and mated. The transgenic offspring of the founder animals may be identified by any method known in the art, such as Southern blot, PCR and expression analysis.

In another embodiment, transgenic fish are created by delivering the modified retrovirus, described above, to single-cell fish embryos. Fertilized fish eggs are collected by any method known in the art. The modified retrovirus is then preferably delivered to the space between the chorion and the cell membrane. This may be accomplished, for example, by loading the modified retrovirus in solution into a glass pipette. The pipette may then be used to pierce the chorion membrane and deliver the viral suspension. Preferably about 50 nL of viral solution is delivered, more preferably about 100 nL of viral solution is delivered, and even more preferably about 200 nL of viral solution is delivered. Injected embryos are preferably returned to a temperature-controlled water tank and allowed to mature. At sexual maturity the founder fish are preferably mated and their progeny analyzed for the presence of the transgene by any method known in the art.

As mentioned above, the methods of the present invention will also prove useful in techniques for identifying genes that are involved in specific biological processes, such as gene trap assays and large-scale mutagenesis screens.

Gene trap experiments allow the identification and cloning of a gene that is expressed in a particular tissue or cell type, and/or at a particular time, based solely on its pattern of expression. Gene trapping relies on the capture of the splicing donor of an mRNA by ectopically inserting a downstream splice acceptor, in this case, carried within an integrated provirus. Gene trapping has been successfully used in several model systems, including the fruit fly *Drosophila*, mammalian cells in culture, and mouse ES cells (which have the advantage of being able to be used to derive mice afterwards for further analysis). Gene trapping in cell culture has the advantage of being fast and inexpensive, but is limited by the inability of the cells to differentiate into specific cell types. Thus, gene trapping experiments in mammalian cell lines in culture usually yield only housekeeping genes expressed non-specifically in any mammalian cell, or cell-specific genes that are only expressed by the particular cell line in vitro. Because cell lines often show incomplete degrees of differentiation, the complement of tissue-specific genes expressed by these cells is limited. Furthermore, there are many tissues for which representative cell lines do not exist.

The use of the above-described recombinant lentiviral vectors for the purposes of gene trapping is facilitated by the self-inactivating mutation in the U3 enhancer element of the 3' LTR. The lack of transcriptional activity from the integrated 5' LTR ensures that any transcription of a reporter element in the provirus is driven by upstream regulatory sequences to the insertion that have been "trapped," rather than from the viral promoter itself.

Thus, one embodiment of the present invention concerns a method of identifying genes that are expressed in a particular tissue and/or at a particular time during the development of an organism. A self-inactivating viral construct is made that preferably comprises a splice acceptor sequence and a sequence encoding a reporter gene. Modified retroviral particles are made using the viral construct as described above and used to infect embryonic cells. Tissues from the founder animal or its progeny are analyzed for the presence of the reporter to determine the temporal and/or spatial pattern of expression. Messenger RNA is collected from the tissues of the animals that express the reporter protein in the time and place of interest. The "trapped" gene may then be identified by any method known in the art. Preferably, oligonucleotides that are complementary to the reporter gene may then used in a reverse transcription reaction to produce a cDNA that contains the sequences of the trapped gene that flank the provirus. The cDNA may then be cloned into a plasmid from which the gene may be identified by nucleotide sequencing.

Gene trap experiments are well known in the art and the skilled artisan would be able to choose the reporter gene, splice acceptor sequence and any other genetic elements that would be useful to include in the viral construct based on the specific analysis that they have undertaken. In addition, by modifying the viral constructs, the technique can be used to trap promoter or enhancer sequences. For promoter trap experiments, the reporter gene lacks any transcriptional regulatory elements, and is only expressed when the virus integrates next to an active promoter. For the enhancer trap, the reporter gene is positioned downstream of a minimal promoter that lacks transcriptional activity, and is only expressed when the virus integrates next to an active enhancer.

Another important paradigm by which biologists study gene function is to disrupt the function of an endogenous gene and, from the mutant phenotype that results, deduce the normal role of that gene in the organism. One way of isolating genes that are important in a particular biological process under study is to perform large-scale mutagenesis to generate animals that are phenotypically mutant in that process and then to isolate the gene that is disrupted in the mutant animal and that is thus responsible for the mutant phenotype. In most such experiments, either radiation or chemicals have been used to induce deletions or nonsense mutations. However, the genes carrying mutations induced by radiation or chemicals are difficult to isolate because no handle is available with which to clone the gene. Rather, these mutations must be identified by positional cloning, a slow and painstaking process in which the mutation of interest is systematically mapped relative to known genetic markers in the genome, with the goal of gradually narrowing down and pinpointing the locus of the mutated gene.

In contrast, a powerful technique that has been used successfully in the fruit fly *Drosophila melanogaster* is that of insertional mutagenesis, in which genes are disrupted when an exogenous piece of DNA is inserted within the coding sequence of the gene. The great advantage of insertional mutagenesis is that, because the sequence of the exogenous disrupting DNA is known, one can directly clone out that piece of DNA and the flanking sequence that corresponds to the gene of interest that has been disrupted. Thus, in contrast to traditional positional cloning strategies used in chemical mutagenesis which may take up to 3 years after the isolation of the mutant, identification and characterization of the mutated gene of interest in an insertional mutagenesis strategy is reduced to just a week or so. The main limitation to the application of insertional mutagenesis in organisms other than the fruit fly is the lack of a DNA element, such as the transposon used in *Drosophila*, that is able to stably integrate and mark its position in the genome at the germline or one-cell embryo stage.

The lentiviral vectors described above can be effective tools for large-scale mutagenesis to identify genes involved in specific biological processes. The modified lentiviruses of the present invention are easily delivered to the germline, and pseudotyping of the viruses with an envelope glycoprotein, such as VSVg, allows the concentration of the virus to extremely high titers. Thus in one embodiment mutagenesis is achieved by delivery of the modified retrovirus to the cell membrane of embryonic cells.

The ability of transgenic animals made by the methods of the present invention to express a gene of interest at high levels suggests that the integrated proviruses are not silenced by methylation. Previous mutagenesis screens using MoLV-based retroviruses have been limited by the observation that, in addition to the provirus, flanking genomic sequences are frequently found to be methylated and inactivated. This methylation complicates the analysis because it becomes difficult to distinguish whether the mutant phenotype is due to the disruption of the gene into which the provirus has inserted, or due to the inactivation of any one of several surrounding genes by methylation.

By delivering modified lentiviruses to embryos according to the methods of the present invention, insertional mutagenesis strategies can be applied to any animal species, including model genetic organisms such as *Xenopus*, zebrafish, mouse, rat, and zebra finch. Early-stage embryos, consisting of several cells, will preferably be targeted because the resulting mosaicism increases the number of unique mutagenic events that can be screened.

The modified lentiviruses integrate randomly into the genome of the target zygotes, including that of the germ cells. Thus, some proportion will disrupt coding sequences. The embryos are preferably raised to sexual maturity, mated, and the progeny are screened for mutant phenotypes of interest. Once a mutant is identified, selective breeding using standard methods is preferably used to isolate the particular insertion(s) responsible for the phenotype.

Once a mutant line is established, the mutated locus is preferably identified using the provirus as a handle for cloning. In one embodiment, an origin of replication and antibiotic resistance gene is included in the viral construct. In this embodiment, genomic DNA from the mutant is preferably isolated, randomly cleaved with an appropriate restriction enzyme, and the linear fragments circularized by ligation. The ligation mixture is then transformed into bacterial cells and plated on antibiotic plates. The plasmid DNA from any colonies that arise is isolated and preferably used as a template for inverse PCR with oppositely oriented, adjacent primers complementary to sequences in the provirus. The amplified DNA molecule(s) is then sequenced to acquire the flanking regions to the integration site, corresponding to the gene(s) mutated.

In another embodiment, inclusion of the tRNA amber suppressor sequence in the provirus allows for the rapid generation of genomic libraries containing the flanking regions of the integration loci, representing the disrupted gene(s). Once these flanking regions are sequenced, they can be compared against the genomic sequence database for that animal to determine candidate gene(s) of interest.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

All patent and literature references cited in the present specification are hereby incorporated by reference in their entirety.

EXAMPLE 1

Transgenic mice were generated that expressed a heterologous protein, green fluorescent protein (GFP). GFP expression was controlled by manipulating the genetic elements in the viral construct employed to create the transgenic mice. For example, a viral construct, FUGW, comprising a ubiquitous promoter was used to produce transgenic mice that expressed GFP in every cell. Inclusion of a nuclear localization signal produced transgenic mice that had GFP localized in the nucleus of their cells. A viral construct with a lymphocyte specific promoter produced mice that expressed GFP in lymphocytes, while a viral construct with a muscle specific promoter produced mice that specifically expressed GFP in muscle cells.

A. Viral Constructs

A viral construct according to the present invention was created using the HR'CS-G plasmid (Miyoshi H, Blomer U, Takahashi M, Gage F H, Verma I M. *J. Virol.* 72(10):8150-7 (1998)). This plasmid is based on the HIV-1 HXB2 proviral DNA (see U.S. Pat. No. 6,013,516).

1. Generation of a Vector Expressing GFP from a Ubiquituous Promoter, FUGW

The HIV-1 flap sequence (SEQ ID NO: 1) was inserted into the HR'CS-G vector. A 147 base pair sequence containing the flap region (Zennou, V., Petit, C., Guetard, D., Nerhbass, U., Montagnier, L., Charneau, P. *Cell.* 101(2), 173-185 (2000)) was PCR amplified from a plasmid encoding the genome of HIV NLA4.3. The 5' PCR primer encoded BglII and PacI sites. The 3' PCR primer contained the BamHI site. The resulting PCR product was digested with BglII and BamHI enzymes and inserted into the BamHI site of the HR'CS-G vector. The resulting plasmid was called Hflap, representing the Hflap sequence that the plasmid contains.

The ubiquitin promoter (SEQ ID NO: 2) was then inserted into the Hflap plasmid. The 1.2 Kb sequence encoding the human polyubiquitin C promoter was excised with BglII and BamHI enzymes and inserted into the BamHI site of Hflap. The resulting plasmid was called HflapUbi, representing the HflapUbi sequence that the plasmid contains.

A multi-cloning site was then inserted into HflapUbi. Two oligonucleotides were designed that encoded the following restriction sites: BamHI HpaI XhoI AscI EcoRI BglII. The oligos were hybridized and inserted into the BamH1 site of HflapUbi. The resulting plasmid was called FUMCS.

A nucleic acid sequence encoding GFP (SEQ ID NO: 3) was then inserted into HflapUbi. The 700 base pair sequence of GFP was digested with BamHI and XhoI and inserted into the XhoI site of HflapUbi, generating HflapUbiG which represents the HflapUbiG sequence that the plasmid contains. The resulting plasmid was called FUG.

Figures 1A, 1B:
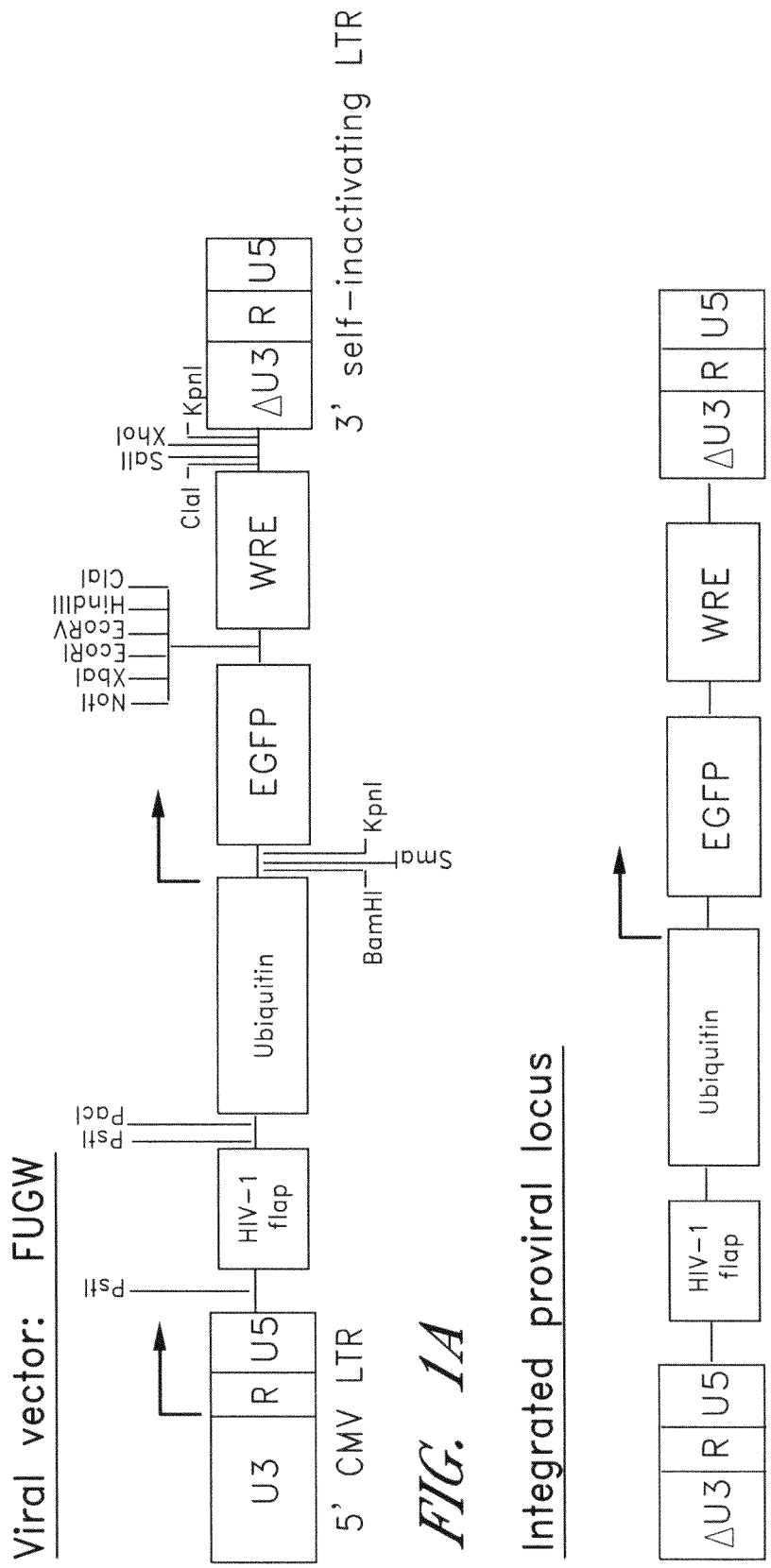
FIG. 1A is a diagram of the FUGW viral construct.
FIG. 1B is a diagram of the provirus that is integrated into the host genome after infection with recombinant virus prepared with the FUGW viral construct of FIG. 1A.

The woodchuck hepatitis virus regulator element (WRE; SEQ ID NO: 4) was then inserted into HflapUbiG. The 500 bp sequence of WRE (Zufferey, R., Donello, J. E., Trono, D., Hope T. J. (1999). *J. Virol.* 73(4), 2886-92) was excised with SalI and XhoI and inserted into the XhoI site of HflapUbiG generating a plasmid containing the HflapUbiGWRE sequence (SEQ ID NO: 8). The resulting plasmid was called FUGW (SEQ ID NO: 9). A map of the FUGW viral vector is presented in FIG. 1A.

2. Generation of a Vector Expressing Nuclear-Localized GFP from a Ubiquituous Promoter, FUH2BGW In order to get specific nuclear localization of GFP, the histone 2B-GFP fusion sequence H2BGFP was cloned into FUGW. The histone 2B-GFP sequence (SEQ ID NO: 5) was digested with SalI and NotI. Both sites were blunted with T4 DNA polymerase and inserted into the HpaI site of FUMCS. The resulting plasmid was called FUH2BGW.

3. Generation of a Vector Expressing GFP from a Lymphocyte-Specific Promoter, FlckGW To achieve lymphocyte specific GFP expression the murine lck promoter (SEQ ID NO: 6) was cloned into the FUGW vector. The ubiquitin promoter from FUGW was removed by excising with PacI and BamH1. The PacI site was blunted using T4 DNA polymerase and the lck promoter was excised with SpeI and BamHI. The SpeI site was blunted using T4 DNA polymerase. The lck promoter was the inserted into the PacI and BamHI sites of FUGW. The resulting plasmid was called FlckGW.

4. Generation of a Vector Expressing GFP from a Muscle-Specific Promoter, FmyoH2BGW To achieve specific expression of GFP in the muscle of transgenic mice the myogenin promoter (SEQ ID NO: 7) was cloned into the FUGW construct. The mouse myogenin promoter was PCR amplified from a mouse genomic BAC. The 5' PCR primer encoded a PacI site, and the 3' PCR primer contained an XbaI site. The PCR product was digested with PacI and XbaI. The ubiquitin promoter was removed from the FUH2BGW vector by cutting with PacI and XbaI. The PacI-BamHI digested PCR product encoding the myogenin promoter was inserted into the PacI and XbaI sites of the FUH2BGW vector.

The constructs described above were then used to prepare recombinant lentivirus. Briefly, replication-incompetent viral vectors, based on the human immunodeficiency virus-1 (HIV-1), were pseudotyped with the vesicular stomatitis virus envelope glycoprotein (VSVg), permitting the virus to be concentrated to very high titers and conferring upon the virus a broad host range. Pseudotyped lentiviruses were produced essentially as described in detail in Yee, J. K., Friedmann, T. & Burns, J. C. (1994). *Methods Cell Biol.* 43, 99-112; Burns, J. C., Friedmann, T., Driever, W., Burrascano, M., and Yee, J. K. (1993). *Proc. Natl. Acad. Sci. USA.* 90, 8033-8037; and Yee, J. K., Miyanohara, A., LaPorte, P., Bouic, K., Burns, J. C., and Friedmann, T. (1994). *Proc. Natl. Acad. Sci. USA.* 91, 9564-9568. Briefly, human fibroblasts 293 cells were transfected with calcium phosphate/DNA coprecipitates of the following plasmids, as described in Gorman, C., Padmanabhan, R. and Howard, B. H. (1983). *Science.* 221, 551-553:

The viral transfer vector described above with self-inactivating LTR;

the HIV-1 packaging vector Δ8.9 (Zufferey, R., Nagy, D., Mandel, R. J., Naldini, L., and Trono, D. (1997). *Nat. Biotechnol.* 15(9), 871-875; Naldini, L., Blomer, U., Gallay, P., Ory, D., Mulligan, R., Gage, F. H., Verman, I. M., and Trono, D. (1996). *Science.* 272(5259), 263-67) with env, vpr, vpu, vif, nef, 5'LTR, 3'LTR, and ψ sequences deleted; and the VSVg envelope glycoprotein.

Viral supernatant was harvested 60 hours post-transfection, subjected to low-speed centrifugation to remove cell debris, filtered through a 0.45 µm nitrocellulose membrane, spun at 25,000 rpm for 1.5 hours to concentrate, and resuspended in a small volume (one hundredth to one thousandth of the original volume) of phosphate-buffered saline (PBS), pH 7.4. The titer of the viral concentrate was approximately $1\times10^6$ pfu/µl as determined in 293 human fibroblasts measured by the number of GFP-positive cells. The viral suspension was stored frozen at −80° C.

B. Production of Transgenic Mice and Rats

The lentivirus was used to produce transgenic mice and rats.

1. Superovulation and Embryo Collection

Female mice and rats were superovulated with a combination of pregnant mare's serum (PMS) and human chorionic gonadotropin (hCG) as described in Hogan, B., Beddington, R., Costantini, F., and Lacy, E. (1994). *Manipulating the Mouse Embryo: A Laboratory Manual*. Cold Spring Harbor Laboratory Press. "Superovulation" refers to administering gonadotropins to female mammals prior to mating to increase the number of eggs that are ovulated. Prepubescent female mice (approximately 25 days of age and weighing between 12.5 and 14 grams) were injected intraperitoneally with 5 IU of PMS (Sigma G 4527, 25 IU/ml in 0.9% NaCl) between 1 and 3 p.m. on day −2, followed by 5 IU of HCG (Sigma C 8554, 25 IU/ml in 0.9% NaCl) 48 hours later on day 0. Prepubescent female rats between 28-30 days of age and weighing between 70 and 80 grams were injected intraperitonally with 25 IU of PMS between 1 and 3 p.m. on day −2, followed by 5 IU of HCG 48 hours later on day 0. For both rats and mice, hormone-treated females were caged overnight with fertile males (2-3 months of age) to mate. On the morning of day 1, females were checked for copulation plugs.

Female mice were sacrificed for embryo collection around 10 a.m. on the morning of day 1, while female rats were sacrificed for collection around 1 p.m. on the afternoon of day 1. Embryos were collected from mice and rats essentially following the procedure described in Hogan, B., Beddington, R., Costantini, F., and Lacy, E. (1994) *Manipulating the Mouse Embryo: A Laboratory Manual*. Cold Spring Harbor Laboratory Press. Briefly, animals were sacrificed by $CO_2$ inhalation, and the oviducts were excised and transferred to a dish containing M2 medium at room temperature. Newly fertilized embryos, enclosed by cumulus mass cells, were released from the swollen ampullae (the upper portion of the oviduct) by gently tugging and opening the walls of the ampullae with fine forceps. The embryos were then transferred to a dish containing a hyaluronidase solution (Sigma H 3884, 300 µg/ml in M2 medium), which enzymatically digested the cumulus cells, thus releasing the embryos. When the cumulus cells were shed, the embryos were transferred to fresh M2 medium to wash off the hyaluronidase solution and preserve the viability of the embryos. In rats, the cumulus cells were found to adhere tenaciously to the surface of some embryos and were difficult to remove completely. Thus in some cases the subsequent experimental manipulations with the zygotes were carried out with some of the cumulus cells still adhering. This did not seem to affect the outcome. The embryos were then transferred to microdrops of M16 medium under mineral oil and cultured in a humidified 37° C. incubator under 5% $CO_2$ until needed.

2. Delivery of Lentiviruses to Single-Cell Embryos

Lentiviruses were delivered to the fertilized oocytes on the same day of collection, targeting only single-cell zygotes to minimize mosaicism. Infection with lentivirus derived from the FUGW viral construct will lead to integration of the provirus locus diagrammed in FIG. 1B. Two different methods were used to deliver the lentiviruses to the embryos:

a. Microinjection of Lentiviruses into the Perivitelline Space of Single-Cell Embryos Micropipettes were prepared by pulling borosilicate glass capillaries (1 mm O.D., 0.7 mm I.D.) on a Sutter Instruments pipette puller. The tip was cut at an angle to approximately 10 µm with a razor blade. The micropipette was then inserted into the pipette holder of a CellTram hydraulic injector (Eppendorf). The lentiviral concentrate prepared above was pipetted up and down to release any large aggregates of cellular debris. The virus was centrifuged at low speed in a tabletop microfuge (1000 rpm for 1 min.), and removed from the top. The viral suspension was then loaded into the micropipette from the tip using gentle negative pressure from the CellTram.

One-cell embryos were transferred to a microdrop of M2 medium on a slide and covered with mineral oil to maintain the osmolarity. The slide was mounted on the stage of an inverted light microscope, and the injection procedure was monitored under 400× magnification. Embryos were held in place against a fire-polished pipette using gentle negative pressure. The pipette holder with the virus was loaded onto a micromanipulator (Leitz). Using the micromanipulator to guide the pipette, the tip was pushed through the zona pellucida into the region between the zona pellucida and the oocyte cell membrane. Using gentle positive pressure, approximately 10 nanoliters of the viral concentrate was delivered into the perivitelline space. The micropipette was then withdrawn from the zygote. After the injection, the embryos were sorted and those that were lysed, abnormal, or at the 2-cell stage were discarded. The remaining embryos were transferred to M16 microdrops under oil and cultured in a 37° C. incubator under 5% $CO_2$ until implantation.

b. Co-Incubation of Denuded Single-Cell Embryos with Lentiviruses

The zona pellucida of the fertilized oocytes was removed by incubation in either an acidic Tyrode's solution (Hogan, B., Beddington, R., Costantini, F., and Lacy, E. (1994). *Manipulating the Mouse Embryo: A Laboratory Manual*. Cold Spring Harbor Laboratory Press) or a 0.5% pronase solution in M2 medium at 37° C. in a humidified 5% $CO_2$ incubator for several minutes. When the zonae appeared to be dissolved, embryos were washed in excess M2 medium and then transferred into 10 µl microdrops of viral suspension under mineral oil. Embryos were cultured individually in separate microdrops to prevent them from adhering to one another. The viral suspension was diluted to various concentrations to roughly control the average number of proviral integrations expected per transgenic genome. Virus in the microdrops was diluted to $2\times10^4$ pfu/µl, 400 pfu/µl, and 8 pfu/µl. Zygotes were incubated in the viral suspension for at least 4-6 hours before implantation to allow viral entry into the cell.

3. Transfer of Embryos into Recipient Females

Timed pseudopregnant females to host the treated embryos were prepared by mating sexually mature females in estrus to vasectomized, mature males the night before the intended day of implantation. Appropriate females were selected from a colony of 30-40 females by taking vaginal smears and examining them for the cell types typical of the estrus phase. Males were vasectomized by tying off the vas deferens at two separate locations, approximately 5-6 mm apart, then cauterizing the intervening segment to sever the tube. Males were vasectomized at least 2 weeks prior to the mating to ensure that all remaining sperm in the genital tract were dead at the time of mating.

Embryos infected with lentivirus were transferred into host females as soon as possible to achieve maximum rates of implantation. Early-stage embryos (0-2.5 days p.c.) with an intact zona pellucida were transferred to the oviduct of timed pseudopregnant females (0.5 days p.c.), while embryos that had reached the morula or blastocyst stage were transferred to the uterus of timed pseudopregnant females (2.5 days p.c.). In general, no more than 30 embryos were transferred bilaterally into the uterus. These procedures were carried out essentially as described in (Hogan, B., Beddington, R., Costantini, F., and Lacy, E. (1994). *Manipulating the Mouse Embryo: A Laboratory Manual*. Cold Spring Harbor Laboratory Press). Pregnancy and delivery of the transgenic litter was as usual.

C. Analysis of Transgenic Animals

Animals in the resulting litters were analyzed for the presence of the transgene and the number of insertions of the transgene by standard Southern blot analysis (Sambrook, J., Fritsch, E. F., Maniatis, T. (1989). *Molecular Cloning: A Laboratory Manuel*. Cold Spring Harbor laboratory Press.), cutting with PstI or BamHI and hybridizing against a GFP+ WRE probe. For constitutive promoters, expression of GFP was determined by directly viewing the skin of the animals under a conventional epifluorescence microscope. Some transgenic animals that were scored as negative for expression were actually expressing the transgene at levels below that of detection by visual inspection with a fluorescent microscope. In such cases, western blot analysis revealed that animals in which GFP fluorescence was not detected by visual inspection did express the GFP protein in some tissues. Similarly, immunocytochemistry proved to be a more sensitive assay for determining expression. For the tissue-specific promoters, some proportion of the transgenic litter was sacrificed during development at embryonic stages, and the translucent embryos were checked for spatially regulated GFP expression under a fluorescent microscope. Expression results were confirmed by histology. To test the ability of the founder animals to transmit the transgene to their progeny, animals positive by Southern analysis were outcrossed to wild-type animals, and their progeny scored for transgenesis and expression as described above.

D. Results

Figure 2:
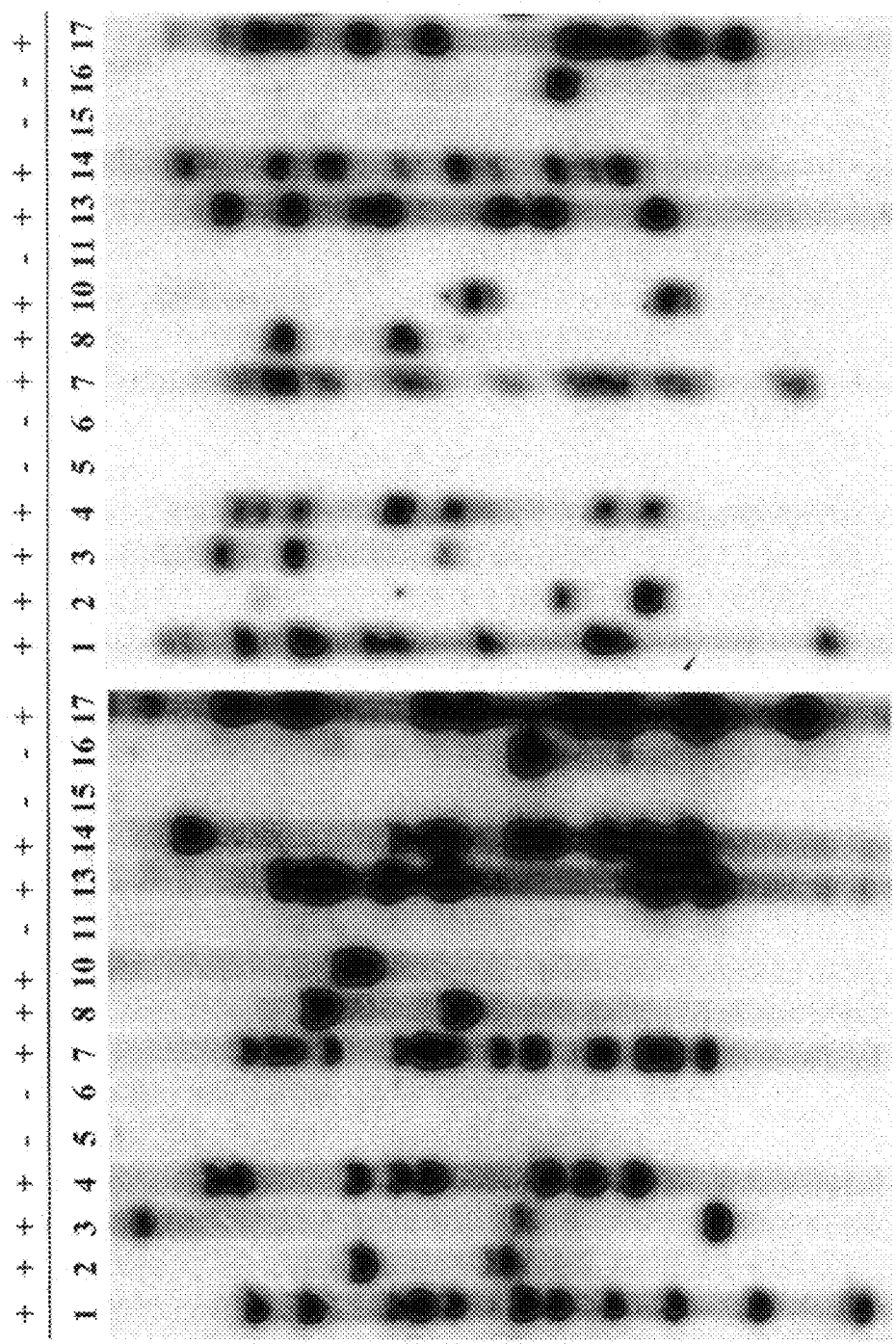
FIG. 2 is a Southern blot analysis of proviral transgene insertions in the founder generation of mice generated by injecting recombinant lentivirus into the perivitelline space of one-cell embryos. Genomic DNA from each animal was digested with either PstI (left) or BamHI (right), and probed with a GFP+WRE sequence. All PstI and BamHI sites in the provirus are located 5' to the GFP gene. Plus signs above each lane indicate GFP expression in the animal detectable by viewing under conventional epifluorescence.

In one set of experiments one-cell mouse and rat embryos were injected in the perivitelline space with recombinant lentivirus as described above. In the first experiment, 17 founder mice developed to term from 78 implanted embryos. Of these, 11 of the 17 founders expressed the transgene as determined by directly viewing the animals under an epifluoresence microscope. Further, 11 of 15 (two, mice died prior to analysis), or approximately 73%, were found to carry the transgene by Southern blot analysis. The average number of insertions in the transgenic mice was 6.1. Several of the animals carried as few as 2 insertions. These results are presented in FIG. 2.

Figure 3:
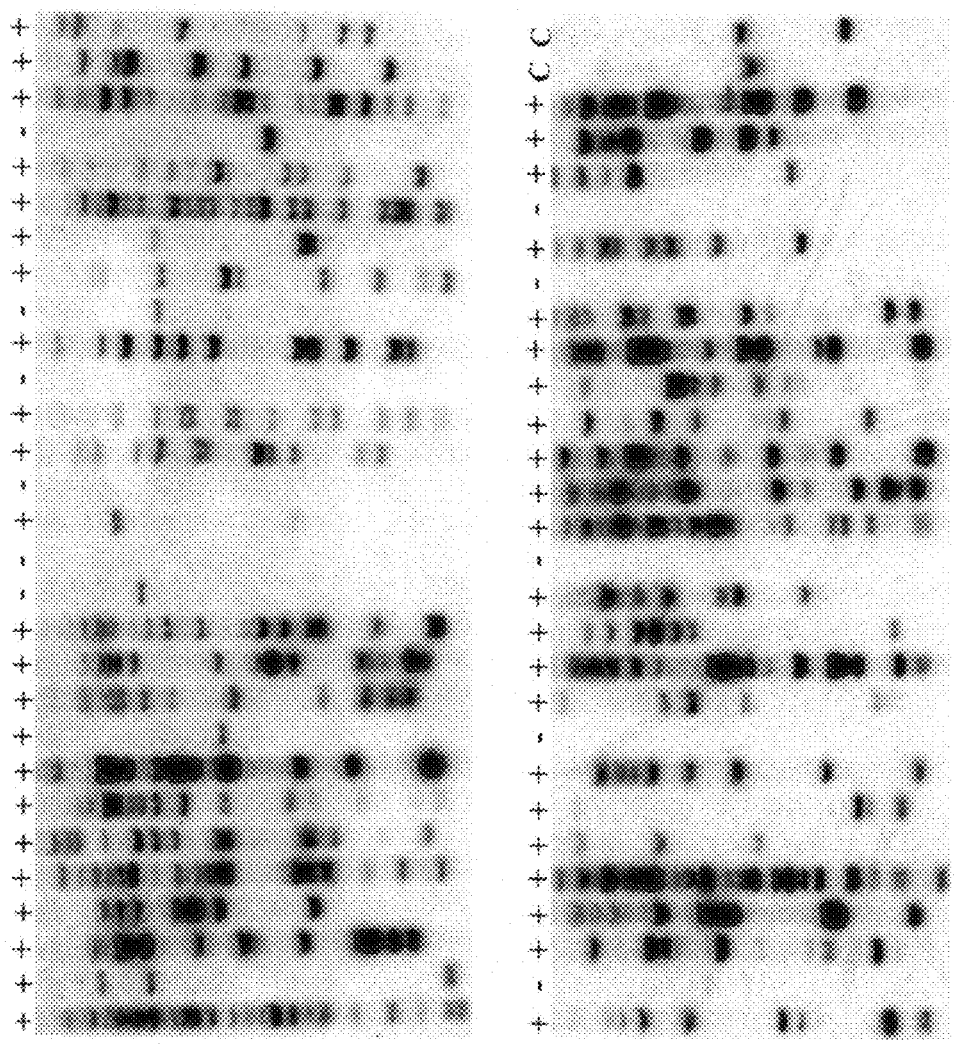
FIG. 3 is a Southern blot analysis of proviral transgene insertions in the founder generation of a second group of mice generated by injecting recombinant lentivirus into the perivitelline space of one-cell embryos. Genomic DNA from each animal was digested with BamHI and probed with a GFP+WRE sequence. All BamHI sites in the provirus are located 5' to the GFP gene. Plus signs above each lane indicate GFP expression in the animal detectable by viewing under conventional fluorescence. Of the 56 founder animals in this experiment, 45 or 80.4% are transgenic. Of these 45 transgenic animals, 41 or 91.1% express GFP at detectable levels. Lanes marked "C" are positive plasmid controls.

In a second experiment, 56 founder mice developed to term from 119 implanted embryos. Of these 45, or about 80%, were found to express the transgene. Thus, in the two experiments 58 out of 73 founder mice, approximately 79.5%, carried the transgene. FIG. 3 shows the Southern blot analysis of proviral transgene insertions in these founder mice.

All GFP-positive mice carried an integrated provirus, and all animals with two or more copies of the provirus expressed the transgene at levels detectable by direct viewing of GFP fluorescence. The intensity of GFP fluorescence correlated positively with copy number, as estimated qualitatively. All major tissues and organs, including skin, bone, skeletal muscle, cardiac muscle, lung, liver, thymus, spleen, stomach, intestine, kidney, brain, retina and gonads were GFP positive.

Figures 4A, 4B:
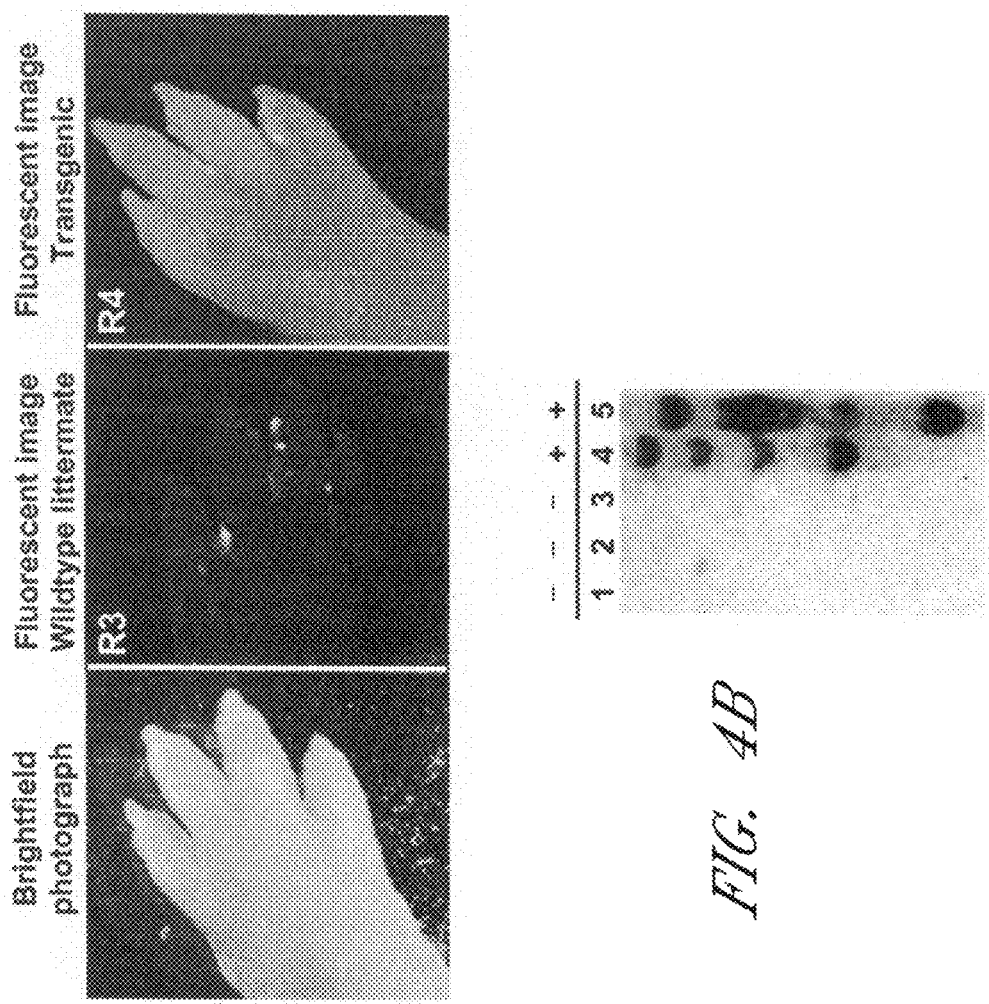
FIG. 4A shows brightfield (BF) and fluorescent images of the paws of newborn rats derived from a FUGW-injected embryo. Pup R4, carrying 4 copies of the proviral insert, expresses GFP in the paw, as well as all other tissues and organs examined. A littermate (R3) carrying no transgene is included for comparison.
FIG. 4B shows a Southern blot analysis of proviral insertions in rats generated by injection of FUGW lentivirus into the perivitelline space of single-cell embryos. Genomic DNA was digested with PstI and hybridized with a GFP+WRE probe. Plus signs above each lane indicate GFP expression in the animal detectable by direct viewing under a fluorescent microscope.

In a third experiment, five rats developed to term from embryos injected with lentivirus created from the FUGW construct. Two of the five rats were found to express the transgene as determined by brightfield and fluorescent images of the paws of the newborn rats (FIG. 4A). Pup R4 expresses GFP in the paw, as well as in all other tissues and organs that were examined (FIG. 4A). FIG. 4B shows the Southern blot analysis of the proviral insertions in these founder rats and indicates that pup R4 carries 4 copies of the proviral insert.

In a continuation of this experiment, out of 22 founder rat pups born from 130 implanted embryos, 13 (59.1%) carried one or more proviral insertions as determined by Southern blot analysis and 9 (40.9%) expressed GFP at levels detectable by directly viewing the skin under a fluorescent microscope. GFP positive founders were crossed to wild-type animals, and F1 progeny rats carrying as few as one copy of the provirus expressed GFP, as determined by direct viewing with a fluorescent microscope, indicating that the GFP-expressing transgene is not silenced by transmission through the germline.

Figure 5:
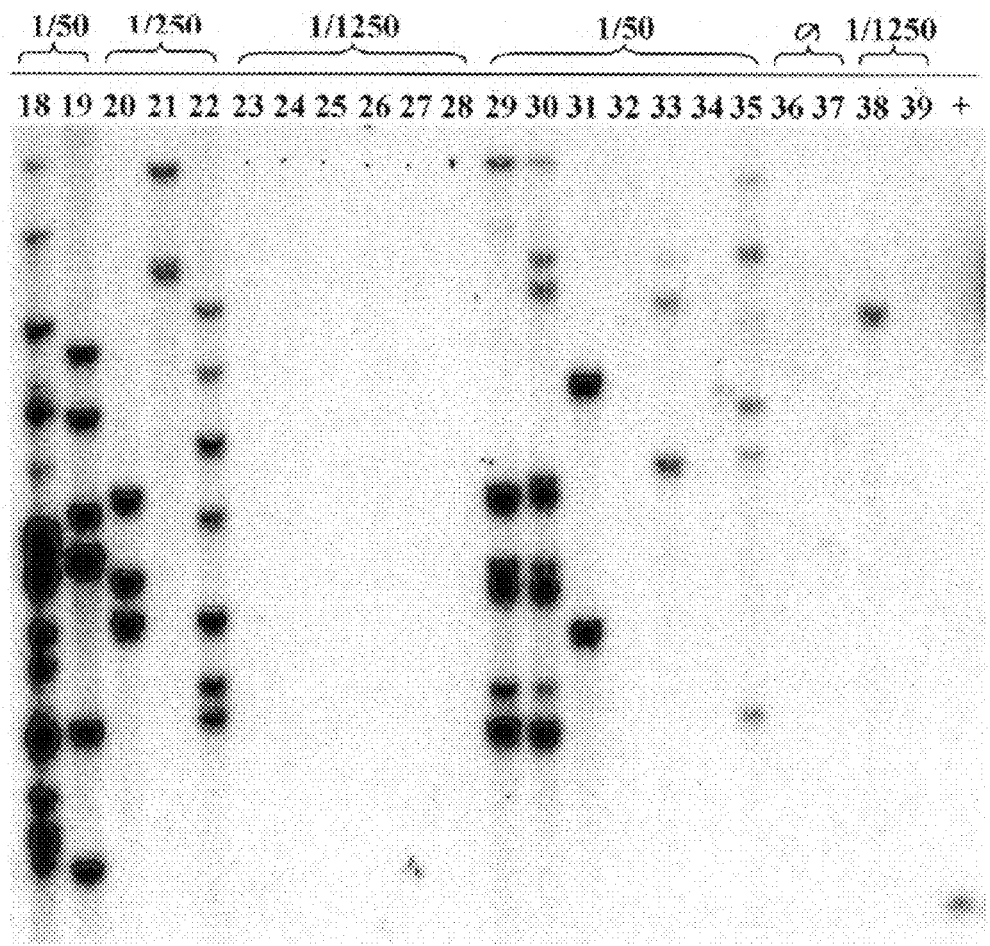
FIG. 5 is a Southern blot analysis of proviral transgene insertions in the founder generation of mice generated by incubating denuded embryos in media comprising recombinant lentivirus produced with the FUGW viral construct. Genomic DNA from each animal was digested with PstI and probed with a GFP+WRE sequence. All PstI sites in the provirus are located 5' to the GFP gene. The ratios above the lanes indicate the dilution of the virus from $1 \times 10^6$ pfu/µl.
Figure 6:
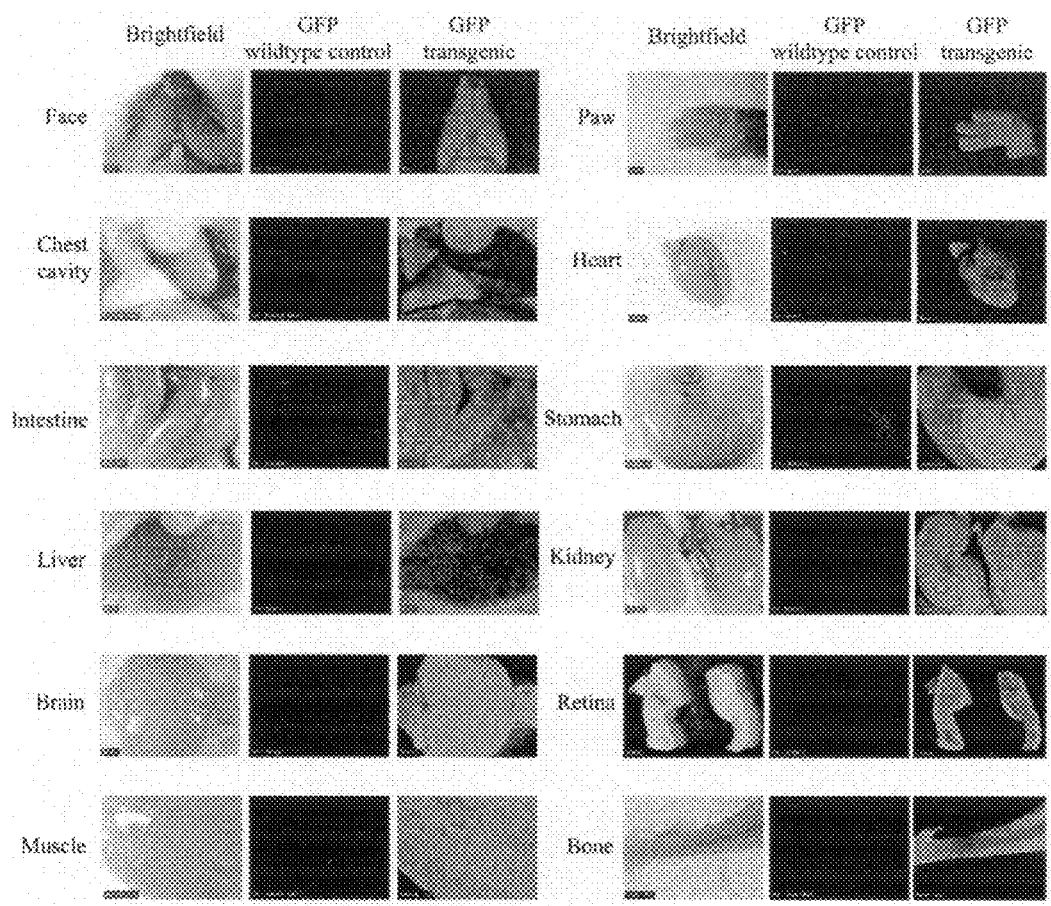
FIG. 6 shows GFP expression in major tissues and organs of a founder mouse. The mouse was perfused intracardially with PBS, pH 7.4, and then 3% paraformaldehyde, and viewed immediately under a fluorescent dissecting microscope. The particular mouse shown was generated by co-incubation of the denuded embryo with the lentiviral suspension and contains 8 proviral insertions. A wildtype animal, identically perfused and photographed is included for comparison.

In another set of experiments denuded mouse embryos were incubated in decreasing concentrations of recombinant lentivirus. A rough correlation was seen between the titer of virus in which embryos were incubated and the number of proviral insertions. At a 1:50 dilution from a stock of $1 \times 10^6$ pfu/µl 5 founder mice that reached term (from 29 implanted embryos) were found to be transgenic. All of these animals carried at least 6 proviral insertions. The average number of insertions was 7.2. Of these, 4, or 80%, were found to express the transgene. At a 1:250 dilution five out of 7 founder mice that reached term (from 18 implanted embryos) were found to be transgenic and express the transgene. In these mice the average number of insertions was 3.8, with two of the animals carrying only one or two copies of the transgene. Finally, at a dilution of 1:1250 only one of the 8 founders (from 40 implanted embryos) was found to be transgenic, with a single insertion. This founder also expressed the transgene. FIG. 5 shows the Southern blot analysis of proviral transgene insertions in these founder mice. FIG. 6 shows GFP expression in one of the founder mice. A second trial with a 1:250 dilution gave comparable results. Eight of 11 founder mice (from 59 implanted embryos) were transgenic, with seven expressing the transgene. The transgenic mice had an average of 2.6 insertions.

Figure 7:
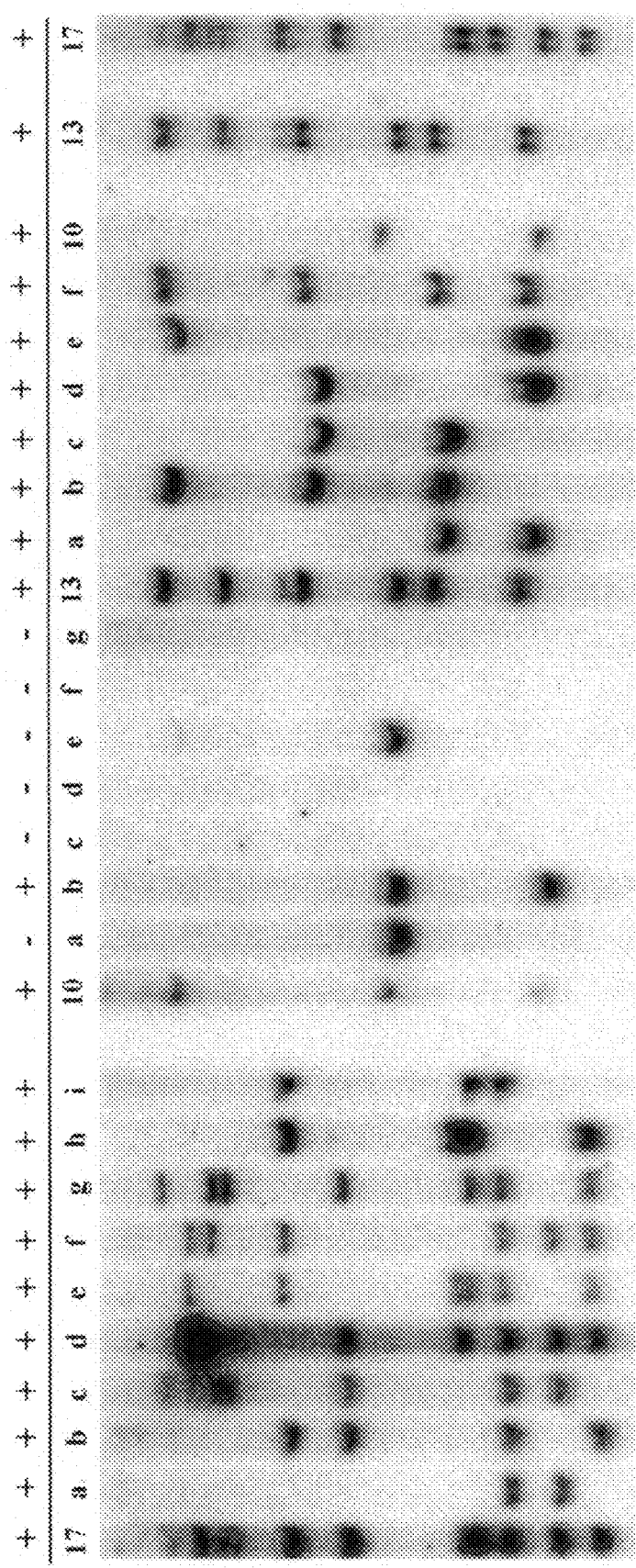
FIG. 7 is a Southern blot analysis of proviral transgene insertions in the F1 progeny of founder transgenic mice, showing that the F1 progeny inherit the proviral transgene in a Mendelian fashion. The founder mice were generated by injection of FUGW lentivirus into the perivitelline space of single-cell embryos. Genomic DNA from each animal was digested with BamHI and probed with GFP+WRE sequence. All BamHI sites are located 5' to the GFP gene. The first numbered lane in each group is the P0 founder animal, while the lettered lanes represent progeny resulting from outcrossing that founder animal to a wildtype animal. Plus signs above each lane indicate GFP expression in that animal detectable by direct viewing of the live animal under a conventional epifluoresence microscope.
Figure 8:
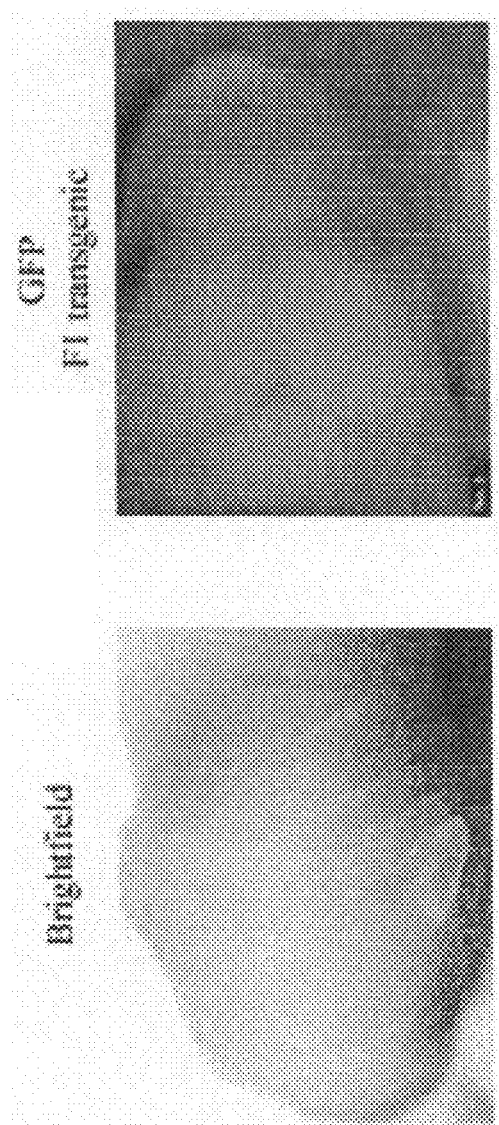
FIG. 8 shows that transgenic mice give rise to transgenic progeny that express the transgene. This indicates that the transgene can go through an entire round of gametogenesis and development without being silenced. Expression of the transgene was determined based on GFP expression in the newborn pup. The pup imaged here is descended from an animal with 10 proviral insertions.

Following outcrossing to wild-type animals, progeny were analyzed for proviral transgene insertions by Southern blot (FIG. 7) and for GFP expression by viewing under an epifluoresence microscope (FIG. 8). As can be seen in Table 1, founder mice were able to transmit the transgene to their progeny. In Table 1, "PV" represents founder transgenics generated by injection of the lentivirus into the perivitelline space of one-cell embryos while "Co-inc" represents founder transgenics generated by co-incubation of the denuded embryos with lentivirus.

TABLE 1

| Founder | No. insertions in founder | No. progeny | No. expressing |
|---|---|---|---|
| PV.13 | 6 | 7 | 6/7 |
| PV.2 | 2 | 4 | 2/4 |
| PV.10 | 2 | 7 | 1/7 |
| PV.17 | 10 | 10 | 10/10 |
| Co-inc.18 | 12 | 12 | 9/12 |
| Co-inc.2 | 0 | 9 | 0/9 |

Ubiquitous GFP expression similar to that of the founder animals was observed in transgenic F1 progeny, indicating that the provirus was not inactivated through one round of gametogenesis and development. All animals carrying two or more insertions of the FUGW provirus expressed GFP at levels detectable by direct fluorescence. However, among transgenic lines carrying one proviral insertion, approximately half expressed the transgene at levels detectable by direct fluorescence. In one single insertion line in which GFP expression was not observed by direct viewing, GFP was detectable by Western blot analysis in some tissues (brain, testes) but not in others (heart, lung, liver, kidney, spleen).

Figure 9:
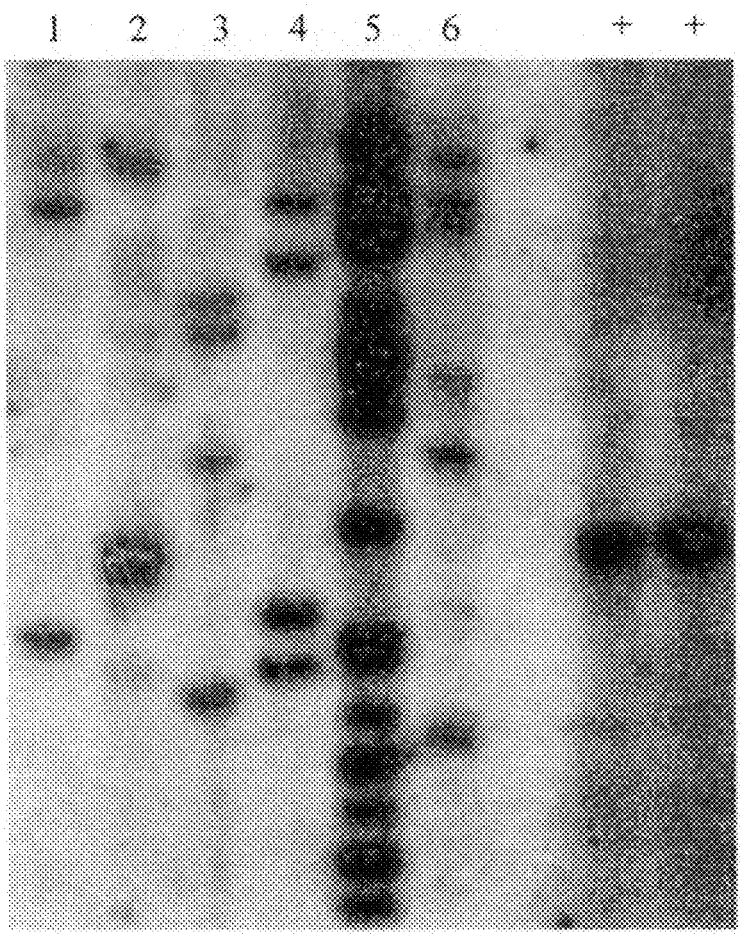
FIG. 9 is a Southern blot analysis of proviral transgene insertions in the founder generation of mice generated using a lentiviral vector containing the myogenin promoter driving a histone2B-GFP fusion. Embryos were recovered from the uterus at embryonic day 11.5 ("E11.5"). The litter consisted of 6 animals, all of which were transgenic. Genomic DNA from each animal was digested with BamHI and probed with a GFP+WRE sequence. A BamHI site is located within the histone2B gene, 5' of the GFP sequence in the provirus. Plus signs above the lanes indicate positive plasmid controls. Animals 5 and 6 were positive for tissue-specific GFP expression at embryonic day 11.5 when viewed as a whole mount under an inverted fluorescent microscope, and animal 5 expressed more highly than animal 6.

In a further experiment, single-cell mouse zygotes were injected in the perivitelline space with recombinant lentivirus derived from the FMH2BGW viral construct described above. This construct comprises a histone2B-GFP fusion gene under the control of the myogenin promoter. The histone2B-GFP reporter was used to concentrate the fluorescence in the nuclei, making the signal more intense. Zygotes were implanted in pseudopregnant female mice and then recovered from the uterus at embryonic day 11.5. As can be seen in FIG. 9, all six founder-mice were transgenic as determined by Southern blot analysis of proviral transgene insertions. Of these, two animals were positive for tissue-specific GFP expression at embryonic day 11.5 (FIG. 9).

Figure 10:
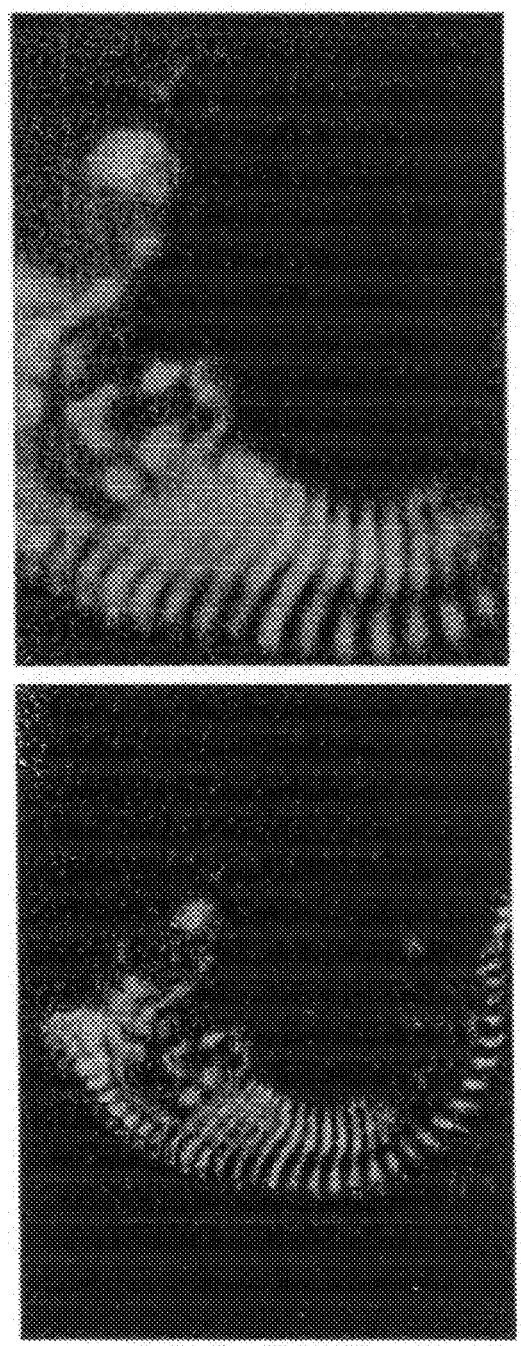
FIG. 10 shows the GFP expression pattern in an E11.5 mouse embryo derived from the perivitelline space injection of lentivirus carrying a histone2B-GFP fusion construct under the control of the myogenin promoter (Yee et al. *Genes and Dev.* 6:1277-1289 (1993)). GFP expression is localized to the somites and can be seen in the emerging muscles in the limb buds, eye and jaw.
Figure 11:
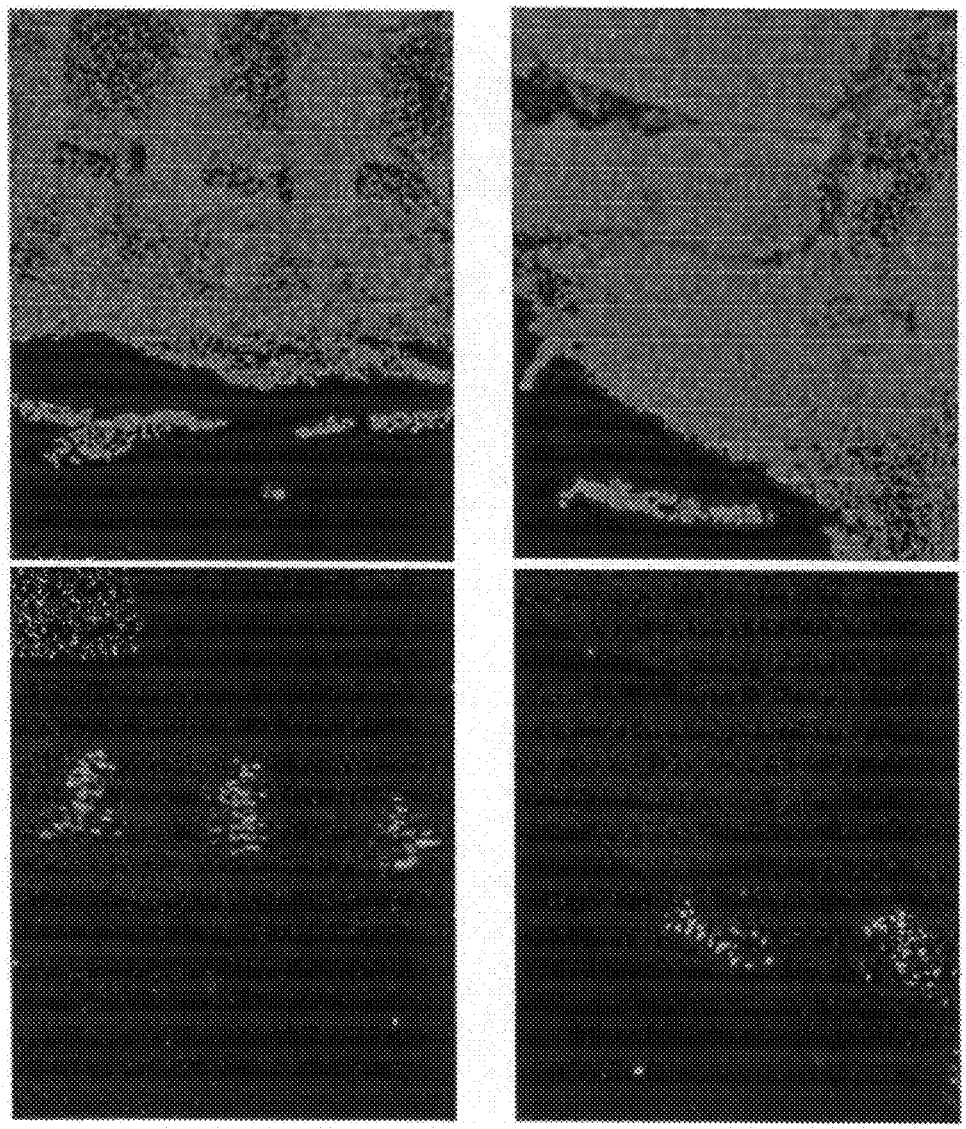
FIG. 11 shows immunofluorescence with an antibody against GFP in a cross-section through an E11.5 embryo carrying the myogenin promoter driving GFP expression. Embryos were derived from single-cell zygotes injected with recombinant lentivirus in the perivitelline space. Embryos were fixed in 3% paraformaldehyde, cryoprotected in 30% sucrose overnight and 30 µm sections were cut on a cryostat. Sections were incubated with a polyclonal antibody against GFP and probed with α-rabbit secondary antibody conjugated to a rhodamine fluorophore. Images on the left are sections as viewed under a rhodamine filter, while images on the right show the nuclear counterstain Hoechst-33342 for each corresponding section. The animal carried 6 proviral insertions of the myogenin-GFP construct. Specific staining of somite tissues can be seen, with the exclusion of the stain from flanking skin and bone tissues.

FIG. 10 shows that at embryonic day 11.5, GFP expression is localized to the somites and can be seen in the emerging muscles in the limb buds, eye and jaw. This expression pattern is consistent with myogenin expression at this stage of development. FIG. 11 shows the results of immunofluorescence studies of sections of an embryonic day 11.5 embryo carrying the myogenin promoter driving GFP. Specific staining of somite tissues can be seen (FIG. 11). FIGS. 12 and 13 show further immunofluorescence studies of cross-sections of an E11.5-embryo carrying a myogenin promoter driving GFP.

Fifteen-day old animals, derived from FMH2BGW-infected zygotes showed GFP fluorescence in the nuclei of skeletal muscle in the tongue, limbs, chest and jaw, but not in cardiac or smooth muscle or other non-muscle tissues examined, reflecting the known specificity of myogenin expression. F1 progeny from three independent founders expressed histone2B-GFP exclusively in the skeletal muscle lineage. Furthermore, progeny carrying as few as one FMH2BGW proviral insertion expressed histone2B-GFP in the appropriate tissue types at high levels detectable by direct viewing with a fluorescent microscope.

In a further experiment, a viral vector containing GFP driven by the T-lymphocyte promoter lck, FlckGW was delivered to the perivitelline space by injection as described above. The resulting transgenic mice expressed GFP exclusively in the thymus.

EXAMPLE 2

Transgenic birds, such as chicken or quail, may be made by the methods of the present invention.

Freshly laid chicken eggs (day 0) are placed in a temperature-controlled, humidified incubator at 38° C. The embryonic blastodisc is gradually rotated to lie on top of the yolk by gently rocking the eggs in the incubator every 15 minutes. A window is opened in the shell and the blastodisc is visualized in freshly laid eggs (0 hours post-laying) or stage X embryos (36 hours post-laying). VSV-pseudotyped lentiviral particles in solution are loaded into a glass capillary micropipette. To maximize the chances of targeting primordial germ cells, virus is injected in the anterior regions of the 0 hour embryos and in the gonadal anlage of the 36 hours embryos. Approximately 200 nL of viral solution are delivered into the space between the perivitelline membrane and the embryonic disk with the aid of a hydraulic injector. The shell window is then closed with a porous tape to allow gas exchange between the embryo and the incubator atmosphere. The embryos are then incubated without rocking. The eggs will hatch after approximately 20 days of incubation time. Hatched chicks are raised to sexual maturity and then mated. The eggs laid by the mated females are raised to hatching and the resulting transgenic chicks are identified, such as by Southern blot, PCR or expression analysis.

EXAMPLE 3

Transgenic zebra finch were made by the methods of the present invention.

Freshly laid zebra finch eggs (day 0) were placed in a temperature-controlled, humidified incubator at 38° C. The embryonic blastodisc was gradually rotated to lie on top of the yolk by gently rocking the eggs in the incubator every 15 minutes. A window was opened in the shell and the blastodisc was visualized. VSV-pseudotyped lentiviral particles in solution were loaded into a glass capillary micropipette. The lentivirus was derived from the FUH2BGW viral construct described above. To maximize the chances of targeting primordial germ cells, virus was injected in the anterior regions of 0 hour embryos and in the gonadal anlage of 36 hour embryos. Approximately 200 nL of viral solution were delivered into the space between the perivitelline membrane and the embryonic disk with the aid of a hydraulic injector.

The shell window was closed with a porous tape to allow gas exchange between the embryo and the incubator atmosphere. The embryos were then incubated without rocking. FIG. 15 shows H2B-GFP expression in the extraembryonic tissue. FIG. 16 shows H2B-GFP expression inside of the zebra finch embryo, indicating that primordial germ cells carried and expressed the transgene.

The eggs will hatch after approximately 20 days of incubation time. Hatched chimeric chicks are raised to sexual maturity and then mated. The eggs laid by the mated females are raised to hatching and the resulting transgenic chicks are identified, such as by Southern blot, PCR or expression analysis.

EXAMPLE 4

Transgenic fish may be made by the methods of the present invention. Breeding pairs of fish are placed in a water tank with a grooved bottom, where fertilized eggs are deposited. Fertilized eggs (zygotes) are collected and held in embryo medium on ice. Zygotes are aligned in grooves formed in a slab of agarose. A modified lentivirus, as described above, is loaded into a glass capillary micropipette. The chorion membrane surrounding the zygote is pierced with the glass micropipette and 200 nL of viral solution are delivered into the space between the zygotic membrane and the chorion. Injected zygotes are returned to a temperature-controlled water tank and allowed to mature. At sexual maturity, the founder fish are mated and their progeny analyzed for the presence of the transgene, such as by Southern blot, PCR and protein analysis.

EXAMPLE 5

The modified lentivirus described above may also be used in gene trap experiments, such as in zebrafish. As discussed above, this technique allows the identification and cloning of a gene that is expressed in a particular tissue or cell type and/or at a particular time based solely on its pattern of expression. Zebrafish is an ideal system for gene trapping for several reasons. First, embryonic development occurs externally, allowing for easy manipulation and viewing of the embryos. Furthermore, early stage zebrafish embryos are translucent, and the pigmentation can be further suppressed for several more days by incubating the embryo in a 0.003% solution of 1-phenyl-2-thiourea (PTU). The translucent property of zebrafish embryos facilitates the viewing of a live fluorescent reporter to identify trapped genes expressed in spatial or temporal patterns of interest.

Self-inactivating lentiviral vectors are engineered to contain a gene trap element consisting of the following sequences: splice acceptor-IRES-GFP-poly A addition signal. This cassette is called SAIGP. The SAIGP element is inserted in a 3' to 5' orientation with respect to the viral LTR sequences, to prevent inappropriate splicing or termination of the viral genome during packaging. Zebrafish zygotes are injected with VSVg-pseudotyped, concentrated SAIGP lentivirus as described above. Fish are raised to sexual maturity and mated. The progeny are viewed with a fluorescent microscope, and GFP-expressing individuals are separated for further analysis. GFP-positive animals are then analyzed with a confocal fluorescent microscope to determine the spatial and temporal pattern of expression. Messenger RNA is extracted from those tissues of the animal that express GFP in the time and place of interest, and reverse transcription with oligonucleotides complementary to GFP yields a cDNA that should contain the sequences of the trapped gene that flank the provirus. The recovered cDNA is subcloned into an appropriate bacterial plasmid, and the gene that has been trapped by the SAIGFP provirus is identified by sequencing the upstream regions of the cDNA.

EXAMPLE 6

Virus particles generated from the FUGW vector were generated as described above. The virus particles were injected using the perivitelline injection method, also described above, into 4 fertilized rhesus monkey (Macaca mulatta) single cell embryos. Monkey oocytes can be fertilized directly with sperm or can be fertilized using the intracytoplasmic sperm injection (ICSI) method. Of the four embryos injected, 2 developed into blastocysts. Both blastocysts were green, evidencing expression of GFP. In the injected blastocysts, cells in the trophectoder (TE) and the inner cell mass (ICM) both were green. Non-injected control embryos were not green. Transformed embryos are transferred to host mothers for gestation. After approximately 150 to 175 days, a newborn rhesus monkey is delivered which expresses GFP throughout. Confirmation of the presence of the transgene and expression in various tissues is carried out as described above.

What is claimed is:

1. A method of producing a transgenic rat comprising:
    transfecting a packaging cell line with:
        a first retroviral construct comprising the R and U5 sequences from a 5' lentiviral LTR, a self-inactivating 3' LTR, a transgene of interest and a promoter operably linked to the transgene of interest;
        a second retroviral construct comprising a packaging vector; and
        an expression plasmid encoding a pseudotyped envelope glycoprotein;
    recovering a recombinant pseudotyped retrovirus from the packaging cell line;
    infecting an oocyte or single cell embryo with the recombinant pseudotyped retrovirus; and
    implanting the oocyte, once fertilized, or single cell embryo in a pseudopregnant female to produce a transgenic rat;
    wherein the pseudotyped retrovirus is integrated into the genome of the transgenic rat, and
    wherein the transgenic rat is able to pass the transgene of interest to a progeny of the transgenic rat such that the progeny expresses the transgene of interest.

2. The method of claim 1 wherein said promoter is an internal promoter.

3. The method of claim 2 wherein the viral construct additionally comprises a reporter gene.

4. The method of claim 3 wherein the reporter gene encodes a fluorescent protein.

5. The method of claim 4 wherein said fluorescent protein is green fluorescent protein.

6. The method of claim 2 wherein the internal promoter is a ubiquitous promoter.

7. The method of claim 6 wherein said ubiquitous promoter is selected from the group consisting of the ubiquitin promoter, the CMV β-actin promoter and the pgk promoter.

8. The method of claim 2 wherein the internal promoter is a tissue specific promoter.

9. The method of claim 8 wherein said tissue specific promoter is selected from the group consisting of the lck promoter, the myogenin promoter and the thy1 promoter.

10. The method of claim 1 wherein said transgenic rat expresses the transgene of interest.

11. The method of claim 1 wherein said packaging cell line is a 293 cell line.

12. The method of claim 1 wherein the 5' LTR sequences are from HIV.

13. The method of claim 1 wherein the self-inactivating 3' LTR comprises a U3 element with a deletion of its enhancer sequence.

14. The method of claim 13 wherein the self-inactivating 3' LTR is a modified HIV 3' LTR.

15. The method of claim 1 wherein the pseudotyped envelope glycoprotein comprises a vesicular stomatitis virus envelope glycoprotein.

16. The method of claim 1 wherein the pseudotyped envelope glycoprotein comprises a mutant ecotropic envelope protein.

17. The method of claim 1 wherein the promoter is operably linked to the R and U5 sequences from the lentiviral 5' LTR.

18. The method of claim 17 wherein the recombinant pseudotyped retrovirus additionally comprises an enhancer operably linked to the promoter.

19. The method of claim 18 wherein the enhancer and promoter are CMV sequences.

20. The method of claim 1 wherein the promoter is a CMV promoter.

21. The method of claim 1 wherein the recombinant pseudotyped retrovirus additionally comprises the woodchuck hepatitis virus enhancer element sequence.

22. The method of claim 1 wherein the recombinant pseudotyped retrovirus additionally comprises a tRNA amber suppressor sequence.

23. The method of claim 1 wherein infecting an oocyte or single-cell embryo comprises injecting the recombinant retrovirus between the zona pellucida and the cell membrane of a rat oocyte or single-cell rat embryo.

24. The method of claim 1 wherein infecting an oocyte or a single-cell embryo comprises removing the zona pellucida from a rat oocyte or single-cell rat embryo and incubating the cell in solution containing the recombinant retrovirus.

25. The method of claim 24 wherein the zona pellucida is removed by enzymatic digestion.

26. The method of claim 1 wherein the packaging vector comprises a HIV-1 packaging vector with the env, nef, 5'LTR, 3'LTR, and vpu sequences deleted.

27. The method of claim 1 wherein the recombinant pseudotyped retrovirus comprises the R and U5 sequences from a 5' lentiviral long terminal repeat (LTR) and a self-inactivating lentiviral 3' LTR.

28. The method of claim 1 wherein infecting an oocyte or single cell embryo with the recombinant pseudotyped retrovirus comprises infecting a single cell embryo.

29. The method of claim 28 further comprising removing the zona pellucida from the single cell embryo.

30. The method of claim 28 wherein infecting a single cell embryo comprises injecting a pseudotyped lentivirus into the perivitelline space of an embryonic cell.

31. A method of producing a transgenic rat comprising the following steps:
    a) removing the zona pellucida from a single-cell embryo;
    b) contacting the single-cell embryo with a pseudotyped retrovirus, wherein the pseudotyped retrovirus comprises a transgene of interest; the R and U5 sequences from a 5' lentiviral long terminal repeat (LTR) and a self-inactivating lentiviral 3' LTR; and
    c) implanting the single-cell embryo in a pseudo-pregnant female to produce a transgenic rat, wherein the transgenic rat is able to pass the transgene of interest to a progeny of the transgenic rat such that the progeny expresses the transgene of interest.

32. The method of claim 31 wherein the pseudotyped retrovirus is a pseudotyped lentivirus.

33. The method of claim 32 wherein the pseudotyped lentivirus is produced by transfecting a packaging cell line with a viral construct.

34. The method of claim 33 wherein the viral construct further comprises an internal promoter.

35. The method of claim 31 wherein the single-celled embryo is contacted with the pseudotyped retrovirus for at least 5 hours.

* * * * *